United States Patent
Rajan et al.

(10) Patent No.: US 12,357,233 B2
(45) Date of Patent: Jul. 15, 2025

(54) SYSTEM AND METHOD FOR CONTEXTUAL DRINK DETECTION

(71) Applicant: HAPPY HEALTH, INC., Austin, TX (US)

(72) Inventors: Nithin O. Rajan, Austin, TX (US); Byron P. Olson, Boone, IA (US); Dustin M. Freckleton, Austin, TX (US); David E. Clift-Reaves, Austin, TX (US); Paulo E. Xavier Da Silveira, Boulder, CO (US); Namita Lokare, Austin, TX (US); Mandy Marie Salinas, Austin, TX (US)

(73) Assignee: ELECTRICITY NORTH WEST PROPERTY LIMITED, Stockport (GB)

( * ) Notice: Subject to any disclaimer, the term of this patent is extended or adjusted under 35 U.S.C. 154(b) by 1049 days.

(21) Appl. No.: 17/269,200

(22) PCT Filed: Aug. 16, 2019

(86) PCT No.: PCT/US2019/046962
§ 371 (c)(1),
(2) Date: Feb. 17, 2021

(87) PCT Pub. No.: WO2020/037298
PCT Pub. Date: Feb. 20, 2020

(65) Prior Publication Data
US 2021/0315522 A1    Oct. 14, 2021

Related U.S. Application Data

(60) Provisional application No. 62/719,535, filed on Aug. 17, 2018.

(51) Int. Cl.
*A61B 5/00* (2006.01)
*A61B 5/0205* (2006.01)
(Continued)

(52) U.S. Cl.
CPC .......... *A61B 5/4875* (2013.01); *A61B 5/0002* (2013.01); *A61B 5/0205* (2013.01);
(Continued)

(58) Field of Classification Search
CPC ... A61B 5/4875; A61B 5/0002; A61B 5/0205; A61B 5/0537; A61B 5/1124;
(Continued)

(56) References Cited

U.S. PATENT DOCUMENTS

2014/0221792 A1 * 8/2014 Miller .................. A61B 5/4875
600/595
2016/0084869 A1 * 3/2016 Yuen .......................... G01P 3/44
73/510
(Continued)

FOREIGN PATENT DOCUMENTS

WO    WO-2017077623 A1 *  5/2017  ......... A61B 5/02438
WO    WO-2017142969 A1 *  8/2017  ............... A61B 5/11
WO    2020037298 A1      2/2020

OTHER PUBLICATIONS

International Search Report & Written Opinion of PCT No. PCT/US2019/046962, mailed Oct. 29, 2019.
(Continued)

*Primary Examiner* — Scott M. Getzow
(74) *Attorney, Agent, or Firm* — Polsinelli PC

(57) ABSTRACT

A system and method operable to monitor hydration and drink activity using one or more body-worn sensors and contextual information to more accurately detect drinking motions made by the user. The system and method can use an application encoded on a non-transitory computer-readable medium to receive disparate data from the one or more sensors to determine if the user has made a drinking motion.
(Continued)

The analysis can be further refined using contextual information and a variable threshold to more accurately identify drinking motions.

36 Claims, 13 Drawing Sheets

(51) Int. Cl.
  *A61B 5/0537* (2021.01)
  *A61B 5/11* (2006.01)
  *A61B 5/1455* (2006.01)
  *G06N 20/00* (2019.01)

(52) U.S. Cl.
  CPC .......... *A61B 5/0537* (2013.01); *A61B 5/1124* (2013.01); *A61B 5/14551* (2013.01); *A61B 5/6802* (2013.01); *A61B 5/7264* (2013.01); *A61B 5/742* (2013.01); *G06N 20/00* (2019.01); *A61B 2562/0219* (2013.01)

(58) Field of Classification Search
  CPC . A61B 5/14551; A61B 5/6802; A61B 5/7264; A61B 5/742; A61B 2562/0219; A61B 5/1123; A61B 5/7282; A61B 5/02405; A61B 5/1112; A61B 5/4809; A61B 5/681; A61B 5/0533; A61B 5/0816; G06N 20/00
  See application file for complete search history.

(56) References Cited

U.S. PATENT DOCUMENTS

| | | |
|---|---|---|
| 2016/0262693 A1 | 9/2016 | Sheon |
| 2017/0188864 A1* | 7/2017 | Drury ................ A61B 5/02427 |
| 2017/0209055 A1* | 7/2017 | Pantelopoulos ... A61B 5/02438 |
| 2017/0220772 A1 | 8/2017 | Vleugels et al. |
| 2017/0290969 A1* | 10/2017 | Millan-Galante ... A61M 1/1613 |
| 2017/0367639 A1 | 12/2017 | Findlay et al. |
| 2020/0152312 A1* | 5/2020 | Connor .................. G06V 20/20 |
| 2021/0315522 A1* | 10/2021 | Rajan .................. A61B 5/4875 |

OTHER PUBLICATIONS

Clapés Albert, et al., "Action Detection Fusing Multiple Kinetics and WIMU: An Application to In-Home Assistive Technology for the Elderly", Machine Visions and Applications, Springer Verlag, DE, vol. 29, No. 5, May 3, 2018, pp. 765-788.

European Search Report; Application No. 19849780.2, mailed Sep. 1, 2021, 11 pages.

Lutze Rainer, et al., "Model Based Dialogue Control for Smartwatches", May 14, 2017, ICIAP: International Conference on Image Analysis and Processing, 17th International Conference, Naples, Italy, Sep. 9-13, 2013, pp. 225-239.

* cited by examiner

SYSTEM AND METHOD FOR CONTEXTUAL DRINK DETECTION

CROSS-REFERENCE TO RELATED APPLICATION

This application is a national stage entry of PCT/US2019/046962 filed Aug. 16, 2019, which claims the benefit of and priority to U.S. Provisional Patent Application No. 62/719,535, entitled "Drink Detection Using Respiration Rate, Inter-Breath Intervals and Inter-Beat Intervals, and Solar Load Used To Improve Fluid Loss Estimation," that was filed in the U.S. Patent and Trademark Office on Aug. 17, 2018, each of which is incorporated herein by reference in its entirety for all purposes.

FIELD

The present disclosure relates to systems and methods related to non-invasive drink detection.

BACKGROUND

Wearable devices have been used by performance athletes and amateurs to monitor physical activities. The devices can be configured to determine a hydration level for the wearer and communicate with a mobile device or external computer to analyze data captured at the devices. Existing methods of hydration and drink detection cannot accurately identify drinking motions or can misidentify other motions as a drinking motion thus underestimating the user's hydration level.

BRIEF DESCRIPTION OF THE DRAWINGS

The following detailed description will be better understood when read in conjunction with the appended drawings. For the purpose of illustration, there is shown in the drawings certain examples of the present disclosure. It should be understood, however, that the present inventive concept is not limited to the precise examples and features shown. The accompanying drawings, which are incorporated in and constitute a part of this specification, illustrate an implementation of apparatuses consistent with the present inventive concept and, together with the description, serve to explain advantages and principles consistent with the present inventive concept.

DETAILED DESCRIPTION

Figure 1A:
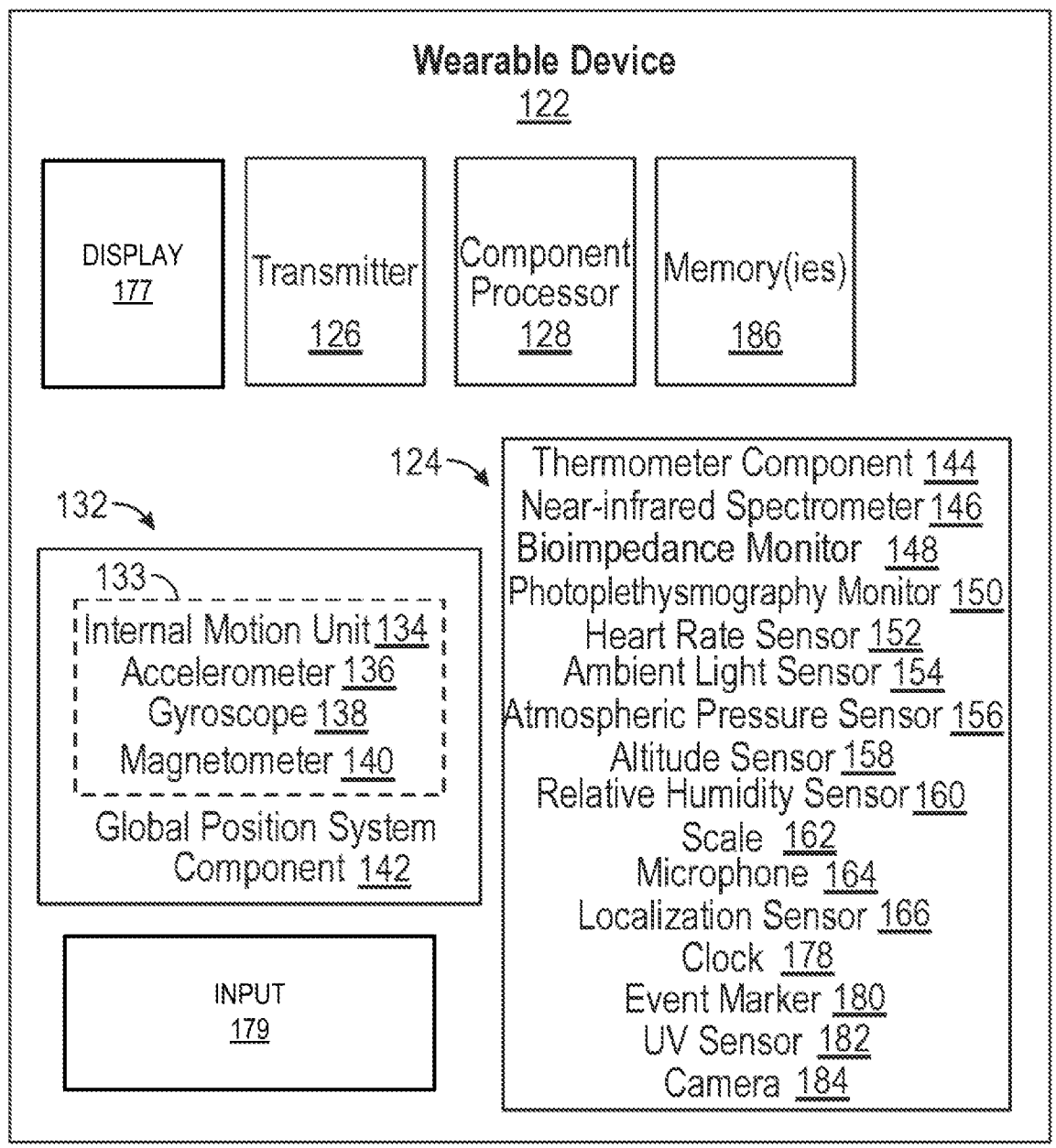
FIG. 1A illustrates an example of a wearable device according to the present disclosure.

Several definitions that apply throughout this disclosure will now be presented. The term "comprising" means "including, but not necessarily limited to"; it specifically indicates open-ended inclusion or membership in a so-described combination, group, series and the like. "About" refers to almost, nearly, on the verge of, or without significant deviation from the numeric representation. For example, about 20 can be 20, or a small deviation from 20. "Coupled" refers to the linking or connection of two objects. The coupling can be direct or indirect. An indirect coupling includes connecting two objects through one or more intermediary objects. Coupling can also refer to electrical or mechanical connections. Coupling can also include linking without physical contact. While "skin" is used throughout the disclosure, any suitable "tissue" of the user can be interchangeably used with "skin."

The present disclosure relates to systems and methods, using data gathered from body-worn sensors, environmental data, and contextual data to detect when a user takes a drink, that and provide information and/or prompt to the user.

In various aspects, the systems and methods use wearable devices configured to communicate with external computing devices, including but not limited to mobile devices, computers, and data servers. In another aspect, the wearable device can include a sensor that is configured to measure motion of the user to detect when a user is drinking a substance. In yet, another aspect, the systems and methods are able to determine if the user should take additional drinks to meet a desired threshold or hydration level.

The present disclosure endeavors to solve a variety of problems in the industry. The present disclosure includes the ability to detect drink events. The present disclosure additionally includes the ability to estimate the volume of liquid ingested by a user during a drink event. The present disclosure also allows the monitoring of the hydration of a user.

The present disclosure includes a system and device for determining drink events using non-invasive techniques. Drink events include drinking fluids, such as water, soda, or any other fluid that the body intakes for hydration.

The present disclosure can be implemented in one or more of the devices and/or systems described herein. In one example, the present disclosure includes a wearable device. As used herein, a wearable device is any device that is in contact or close proximity to a user of the device. Examples of wearable devices include a wrist worn device, arm, hand and/or finger worn device, clothing, an athletic aid, a monitor, a bracelet, a band, a ring, and/or compression sleeves. The wearable devices can be configured to have a wireless communication or wired communication interface to allow for exchange of data. In at least one example, the wearable device is operable to be electronically coupled to a mobile device. In at least one example, the wearable device can be configured to include a user notification component that provides instructions to the user. The user notification component can be a display, an audio device, a vibration device, and/or a visual indicator. In other examples, the user notification component can be omitted and the wearable device can communicate instructions to the mobile device for communication of the instructions to the user.

The term mobile device can include a device that has a processor and a memory. The mobile device in at least some examples includes a display. Additionally, the mobile device can include a communication component that is operable to allow for communication with the mobile device to an external device. The wearable device can also be configured to communicate with one or more external sensor components. The wireless communication can be performed using short range wireless communication protocols such as BLUETOOTH, ZIGBEE, Advanced and Adaptive Network Technology (ANT+), WI-FI, Radio Frequency Identification (RFID), or the like.

Maintaining proper hydration is important not only to assure that athletes can maintain peak performance but also to maintain one's good health, cosmetic appearance, and/or wellness. Proper hydration is important to keep cognitive function and/or to help manage one's weight. It is also critical in maintaining one's good health, including preventing headaches, coronary heart disease, kidney stones, and/or cancer.

Hydration maintenance is best achieved under long-term and/or continuous monitoring of vital signs, rendering it a task that is best performed by a device that is in prolonged contact with the user, such as a wearable device. Moreover, wearable devices are capable of integrating a large range of sensors and/or a processor, storing the signals generated by these sensors in its internal memory for later processing and/or communicating these signals, and/or the results of its internal processing. The signals can also be communicated to the user and/or to the world at large via wireless (or wired) communications, including storing data in the cloud for visualization, for further processing by a server, and/or for storage in a larger database, making aggregate data available to additional processing and/or to the development of new algorithms.

Maintaining proper hydration requires estimating the balance between fluid gains and/or fluid losses. That is to say, by monitoring drinks one can estimate the input side of hydration monitoring, resulting in the health and/or wellness benefits commonly associated with the maintenance of proper hydration.

In an example, a mobile device system includes a mobile device and/or a wearable device operable to detect drink events and/or monitor hydration for a user. The mobile device has at least one sensor which can detect motion of the mobile device. The wearable device can detect a biological indicator of the user and can transmit the data to the mobile device. The mobile device and/or another component in the system correlates the biological indicator of the user with the detected motion signal(s) in time to determine if one or more drink events has occurred and creates an input log for each drink event. In at least one example, the mobile device also determines a net balance of the user based on the input logs and/or output logs for expelled fluids by, for example, vomiting, urination, defecation, and/or perspiration. The net balance can provide the benefit of helping to improve the health and/or well-being of a user by being within a predetermined range, below, or above a predetermined threshold. For example, the net balance can be used to help a user to reach health-related goals such as, for example, staying well hydrated. To be well hydrated, a user should be above a hydration threshold. Although the system and/or device are described with respect to a mobile device, the system and/or device can be entirely operable on a wearable device.

In another example, a wearable device operable to detect drink events of a user includes at least one motion sensor operable to detect motion and/or record motion signals of the wearable device. The wearable device can further include a processor coupled to the at least one motion sensor and/or at least one biological sensor coupled to the processor and is operable to detect one or more biological indicators of the user. The wearable device can also include a memory that is operable to store instructions to cause the wearable device to do one or more of the following: obtain at least one biological indicator of the user, correlate the biological indicator of the user with the detected one or more motion signals, and determine that a drink event is detected based on the correlation between the detected motion signals and/or the at least one biological indicators.

In another example, a mobile device can be coupled with the wearable device and can include a processor. The mobile device can also include a display coupled to the processor and operable to display data received from the processor. The mobile device can also include a memory coupled to the processor and operable to store instructions to cause the processor to do one or more of the following: obtain, from the wearable device, at least one of the one or more biological indicators of the user, correlate the at least one biological indicators of the user with the detected one or more motion signals, and determine that a drink event is detected based on the correlation between the detected one or more motion signals and/or the at least one biological indicators.

FIG. 1A illustrates an example of a wearable device 122 according to the present disclosure. The wearable device 122 can include a transmitter 126, a component processor 128, one or more biological sensors 124, a display 177, and input device 179, a memory 186, and/or one or more additional sensors 132. The wearable device 122 can include and/or be coupled with at least one external sensor component which can be one or more of: scales, water bottles, glucose measurement systems, blood pressure monitors, pulse oximeters, respiration rate monitors, tissue oximeters, respirators, electrocardiogram monitors, and/or the like. The wearable device 122 can also be enabled to wirelessly communicate with other devices.

The one or more biological sensors 124 can be coupled to the component processor 128 and is operable to detect a biological indicator 206 of a user 208. The transmitter 126 is operable to transmit a detected biological indicator 206 to the at least one communication component 118 of the mobile device 100, a remote computer 168, and/or another external device. The biological sensors 124 can include one or more of a thermometer component 144 operable to measure a temperature of skin of the user 208 and/or surrounding ambient temperature, a near-infrared spectrometer (NIRS) 146 operable to monitor chromophores that constitute a tissue of the user 208, a bioimpedance monitor 148, a photoplethysmography (PPG) monitor 150, a heart rate monitor 152, an ambient light sensor 154, an atmospheric pressure sensor 156, an altitude sensor 158, a relative humidity sensor 160, a scale 162, a microphone 164, a localization sensor 166, a clock 178, an event marker 180, a ultra violet (UV) sensor 182, and/or a camera 184. Furthermore, the one or more biological sensors can be operable to detect one or more biological indicators, which can include a heart rate, a heart rate variation, a blood pressure, a respiration rate, a blood oxygen saturation level, muscle oxygenation level, skin temperature, skin perfusion, skin impedance, galvanic skin response, blood pressure, tissue perfusion, blood flow, blood volume, extracellular fluid, tissue hydration, tissue hydration variation, intracellular fluid, photoplethysmograph, images, videos and/or sounds associated with a drink event. For example, the signals of a PPG monitor can be processed to measure blood oxygen saturation, heart rate, heart rate variation, blood pressure and/or respiration rate. As such, a PPG monitor can have the function of multiple individual sensors, and the device 122 can be more compact.

The additional sensors 132 include one or more motion sensors 133. The motion sensors 133 can include an inertial motion unit (IMU) 134, an accelerometer 136, gyroscope 138, and/or magnetometer 140. The additional sensors 132 can also include a global position system component 142 to assist in determining a physical location of the user.

Figure 1B:
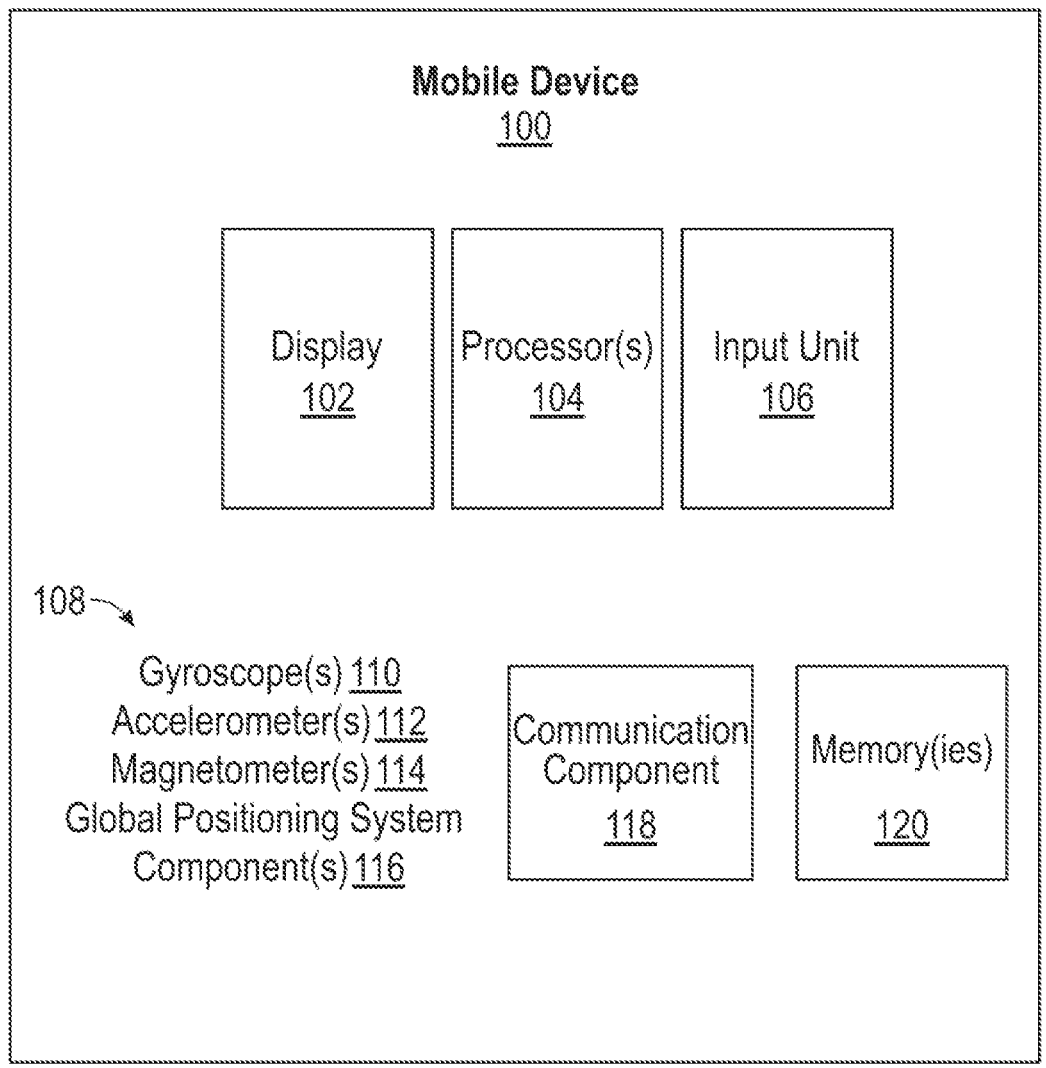
FIG. 1B illustrates an example of a mobile device according to the present disclosure.

FIG. 1B illustrates an example of a mobile device 100 according to the present disclosure. The mobile device 100 includes a display 102, a processor 104, an input unit 106, at least one sensor 108, at least one communication component 118, and/or a memory 120. The at least one sensor 108 is operable to detect motion of the mobile device 100. The at least one sensor 108 can be a gyroscope 110, an accelerometer 112, a magnetometer 114, and/or a global positioning system component 116. The at least one communication component 118 is operable to receive and/or transmit data from a wearable device 122 and/or a remote computer 168. The processor 104 is coupled to the at least one sensor 108 and/or the at least one communication component 118.

Figure 1C:
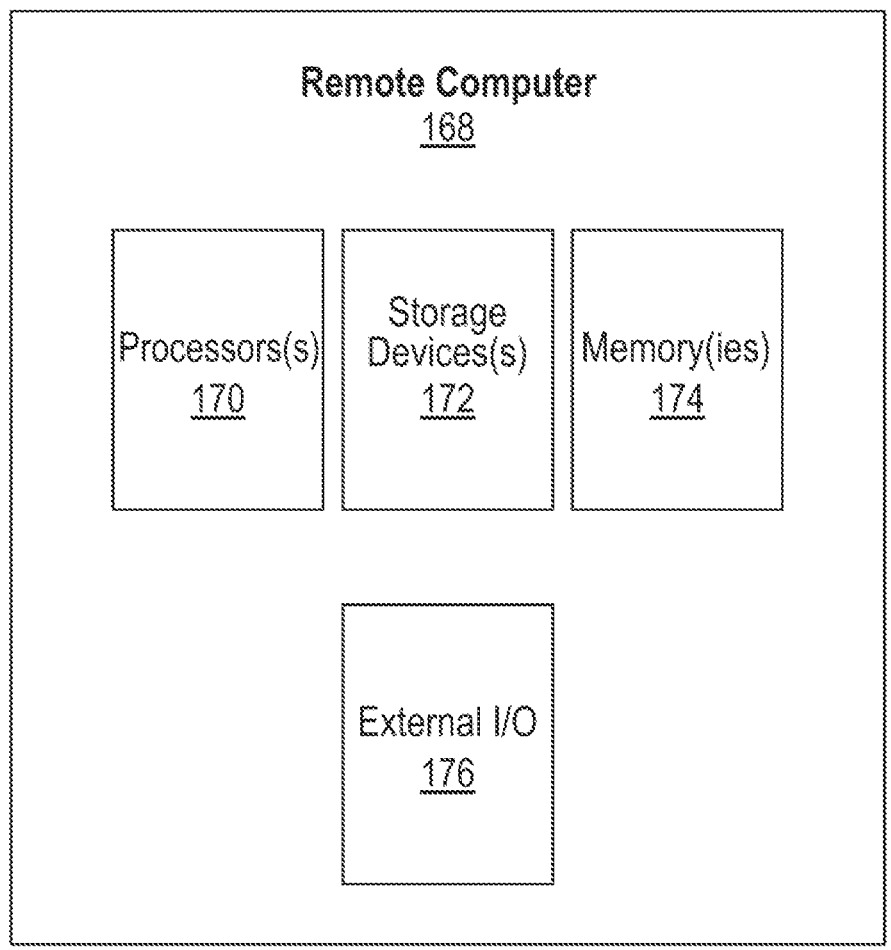
FIG. 1C illustrates an example of a remote computer according to the present disclosure.

FIG. 1C illustrates an example of a remote computer 168. The remote computer 168 can include one or more of: one or more processors 170, one or more storage devices 172, one or more memories 174, or one or more external Input/Output (IO) interfaces 176. The remote computer 168 can be a cloud based computer system 212, shown in FIG. 2 or a cloud storage and data processing system 105, shown in FIG. 1D.

Figure 1D:
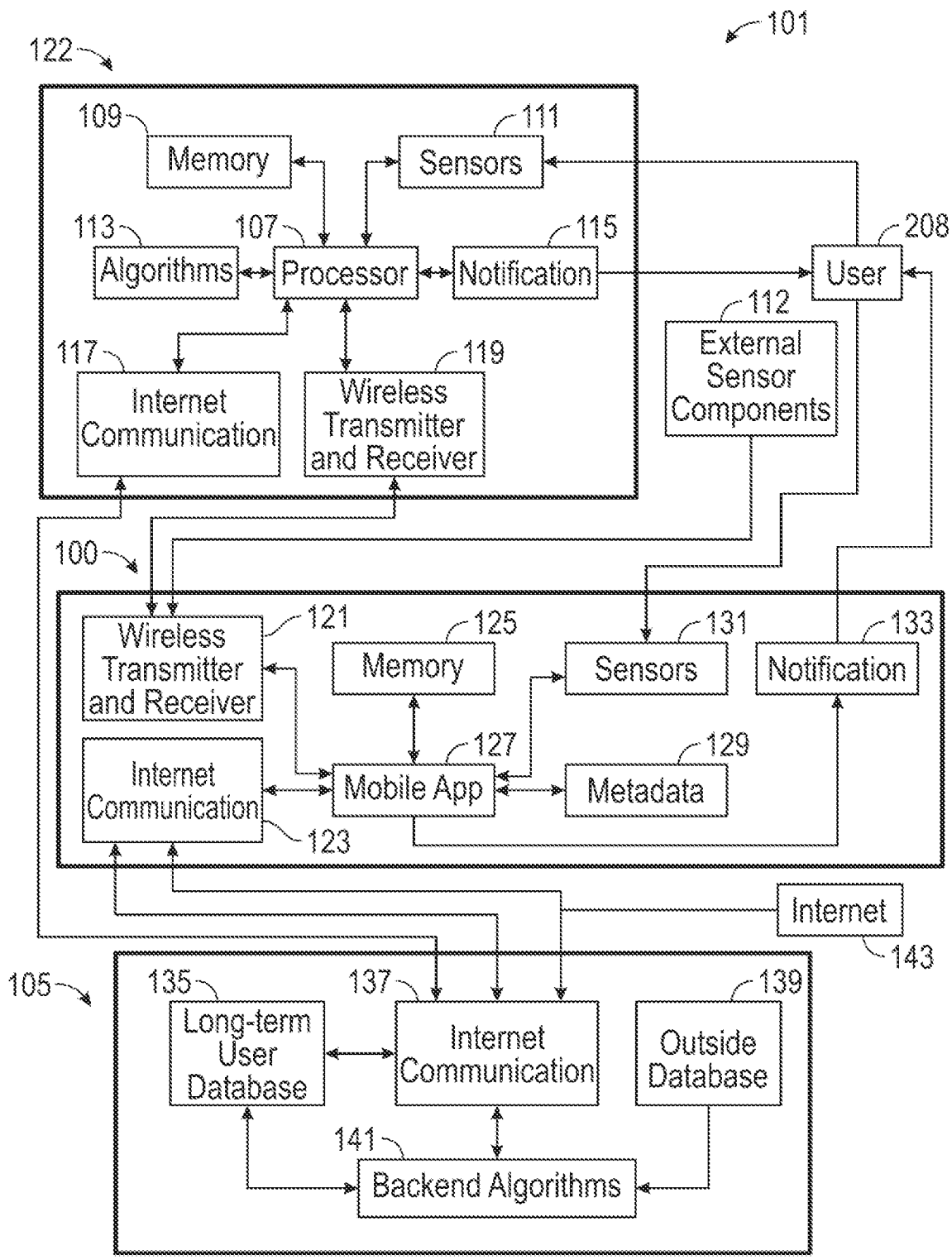
FIG. 1D is a schematic diagram of an example wearable device system according to the present disclosure.

FIG. 1D is a schematic diagram of an example wearable device system 101 according to the present disclosure. The wearable device system 101 can include the mobile device 100, the wearable device 122, and/or a cloud storage and data processing system 105. In at least one example, the cloud storage and data processing system 105 can include one or more of the components described in relation to the remote computer 168 of FIG. 1C. Further, an internet 143 is operable to allow communication between the mobile device 100, the wearable device 122, and/or the cloud storage and data processing system 105. The wearable device 122 can include one or more of: a processor 107 operable to communicate with a memory 109, one or more sensors 111, one or more algorithms 113, internet communication 117, and/or a wireless transmitter and receiver 119.

The internet 143 can refer to the Internet, an intranet, and/or another wired or wireless communication network. For example, the internet 143 can include a Mobile Communications (GSM) network, a code division multiple access (CDMA) network, 3rd Generation Partnership Project (GPP) network, an Internet Protocol (IP) network, a wireless application protocol (WAP) network, a WiFi network, a satellite communications network, and/or an IEEE 802.11 standards network, as well as various communications thereof. Other conventional and/or later developed wired and/or wireless networks can also be used.

In one example, the one or more sensors 111 collects data from a user 208 and the processor 107 processes the data and sends at least one notification 115 to the user 208. The at least one notification 115 can be provided to the user 208 via one or more of a display, lights, sound, vibrations, and/or buzzers. The at least one notifications 115 can further be associated with achieving one or more predefined goals, wherein the one or more predefined goals are health or well-being. In one example, the predefined goal can be to improve well-being by maintaining a level of hydration in order to increase a user's overall health. In another example, the predefined goal can be to stay hydrated within an allowable range of net hydration balance, thus preventing disease states related to dehydration. In other examples, the predefined goal can include one or more goals, which can be both diet and/or exercise related. In other examples, the predefined goals can include skin beauty and/or mental alertness goals. In other examples, the predefined goals can include athletic performance goals, such as pre-hydrating in preparation for a given athletic event.

The mobile device 100 includes a mobile application 127 operable to communicate with one or more of a memory 125, a wireless transmitter and receiver 121, a metadata 129, a one or more sensors 131, and an internet communication 123. In an example, the mobile device 100 is controlled by the mobile application 127 that collects additional data from the one or more sensors 131 and also collects the metadata 129. The metadata 129 can be, for example, from one or more of a user's calendar, contacts, and/or geographic location.

The cloud storage and data processing system 105 can include one or more backend algorithms 141 operable to communicate with a long-term user database 135, one or more outside databases 139, and/or an internet communication 137. The cloud storage and data processing system 105 enables the storage of long-term user data into the long-term user database 135 and/or the execution of more complex backend algorithms 141. These backend algorithms 141 also benefit from the long-term data derived from other users that are similar to a specific user. The information derived from the backend algorithms 141 are provided to the user 208 via the mobile application 127 and/or directly to the wearable device 122.

The memory of the mobile device 100, the one or more wearable devices 122, the remote computer 168, the cloud-based computer system 212, and/or the storage device 214, can include volatile and/or non-volatile memory, e.g., a computer-readable storage medium such as a cache, random access memory (RAM), read only memory (ROM), flash memory, and/or other memory to store data and/or computer-readable executable instructions such as a portion and/or component of the drink detection application 702.

Furthermore, The memory of the mobile device 100, the one or more wearable devices 122, the remote computer 168, the cloud-based computer system 212, and/or the storage device 214 can be volatile media, nonvolatile media, removable media, non-removable media, and/or other media or mediums that can be accessed by a general purpose and/or special purpose computing device. For example, the memory section 508 can include non-transitory computer storage media and/or communication media. Non-transitory computer storage media further can include volatile, non-volatile, removable, and/or non-removable media implemented in a method and/or technology for the storage (and retrieval) of information, such as computer/machine-readable/executable instructions, data and/or data structures, engines, program modules, and/or other data. Communication media can, for example, embody computer/machine-readable/executable, data structures, program modules, algorithms, and/or other data. The communication media can also include an information delivery technology. The communication media can include wired and/or wireless connections and/or technologies and can be used to transmit and/or receive wired and/or wireless communications.

Figure 2:
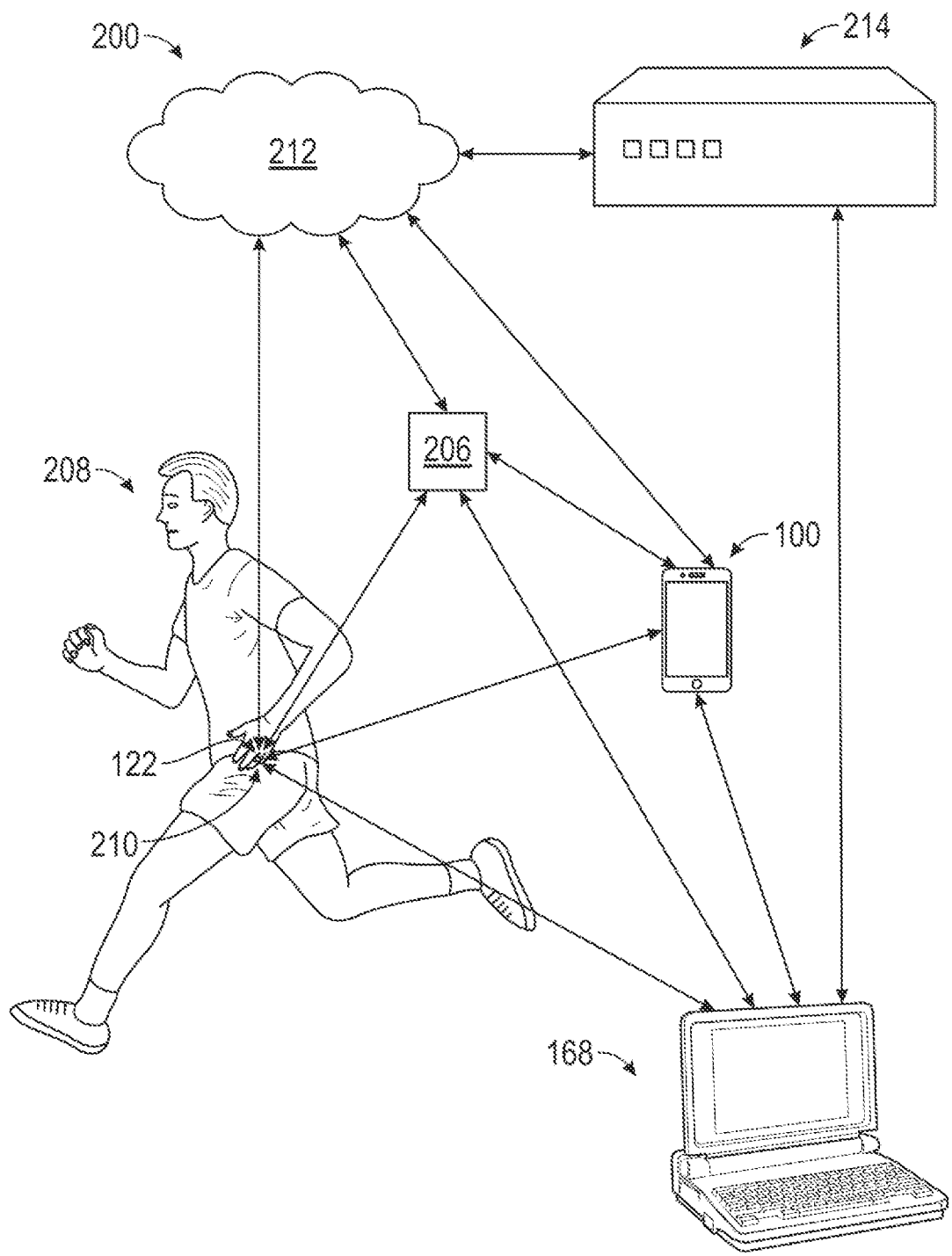
FIG. 2 is a schematic diagram of an example mobile device system according to the present disclosure.

FIG. 2 illustrates an example mobile device system 200. The mobile device system 200 can include a mobile device 100, one or more wearable devices 122, a remote computer 168, a cloud-based computer system 212, and/or a storage device 214. The components can communicate with each other as indicated by the arrows shown. For example, the mobile device 100 can communicate with one or more of the cloud based computer system 212, the remote computer 168, and/or the one or more wearable devices 122.

In one example according to the present disclosure, the one or more wearable devices 122 can be in the form of a wrist device 210 operable to be worn on a wrist of a user 208. The wrist device 210 can also include additional sensors 132 (shown in FIG. 1A) to measure motion of a wrist and/or record motion signals corresponding to the measured motion.

The motion sensors 133 provide the wearable device 122 with a set of motion signals indicative of the position and/or motion of the limb in which the wearable device 122 is worn—typically the wrist. The motion signals are then processed, for example, either by the IMU and/or by the processor, to generate a new signal indicative of significant motion. For example, the motion signal can include the sum of the squares of the accelerations measured in the x, y and/or z axes of the accelerometer present in the IMU. Once the motion signal is detected above a certain threshold level (for example, at least 1.5 times higher than the level of motion detected when the user is at rest) the wearable device 122 processes the other signals, for example additional x, y, and/or z accelerations, provided by the motion sensors 133 in order to identify the motion being undertaken by the user.

Drinking motions often consists of the user moving his/her dominant arm toward their mouths. To prevent confusing drinking motions with other similar motions a library of motions can be created by having a number of users perform similar motions in a large number of trials. The motions are labeled and identified as to what motions they represent at a given point in time and with a given duration. As such, machine learning classification algorithms, such as k-nearest neighbors, support vector machines, decision tress, time-delay neural networks, linear and/or quadratic discriminant analysis, can be used to distinguish between true drinking motions from other (false-positive) motions. The resulting classifier algorithms and their pertinent parameters can be loaded onto the wearable device memory 186 and the algorithm is executed by the processor 128 whenever a significant motion is detected, resulting in a new signal indicative of a drinking motion.

In various embodiments, the method for the detection for drinking uses data acquired from both motion sensors and/or optical sensors, such as but not limited to the motion sensors 133 and the PPG sensor 150, respectively.

In at least one example, the detected motion signals then can be transmitted to the mobile device 100 and/or remote computer 168. The wrist device 210 can also be operable to communicate with the mobile device 100 and/or other connected device via a wired and/or wireless communication connection. For example, the wrist device 210 can wirelessly communicate with the mobile device 100, the remote computer 168, and/or a cloud based computer system 212 indicated by the arrows shown in FIG. 2. In another example, the wrist device 210 can communicate with the mobile device 100, the remote computer 168, and/or the cloud based computer system 212 via a wired connection. The wrist device 210 can be entirely self-sufficient. In other examples, the wrist device 210 can be without a connection to the internet and/or mobile device 100. The data transmitted to the cloud based computer system 212 and/or other long-term memory storage device can be stored for future use and/or processed to provide information useful to a user 208.

The memory 120 of the mobile device 100 can be operable to store further instructions to cause the mobile device 100 to display a recommendation to the user 208 for a next drink event that includes an input activity, an input timing, and/or an input duration. In at least one example, the wearable device 122 can display the information without the presence of the mobile device 100. For example, the mobile device 100 and/or wearable device 122 can display instructions to drink two ounces of water in about five minutes while a user 208 is running. Furthermore, the memory 120 of the mobile device 100 can cause the mobile device 100 to display a determined drink event on a display of the mobile device and receive confirmation and/or modification of the displayed drink event. Also, the display 102 can display data received from the remote computer 168, the cloud based computer system 212, and/or the one or more wearable devices 122.

The display 102 can also display an output event that includes one or more of: output activity, output timing, and/or output duration. The output events can be perspiration, urination, defecation, excretion, coughing, sneezing, vomiting, blood loss, plasma loss, ascetic fluid loss, fluid redistribution, diarrhea, temperature loss, temperature change, insensible fluid loss, fat loss, muscle loss, bone loss, calories burnt, sleep loss, attention loss, alertness loss, yelling and/or crying (indicators of mood loss or the like).

Furthermore, the net balance of input and/or output can be displayed. The long-term monitoring of the net balance of input events and/or output events can be used by the mobile device 100 and/or wearable device 122 to provide the user 208 with relevant information regarding their health, wellness, and/or cosmetic appearance. The beneficial information includes hydration balance. For example, the mobile device 100 and/or the wearable device 122 can use sensed estimates of drink events and/or fluid intake to notify the user to continue drinking fluid.

Figure 3A:
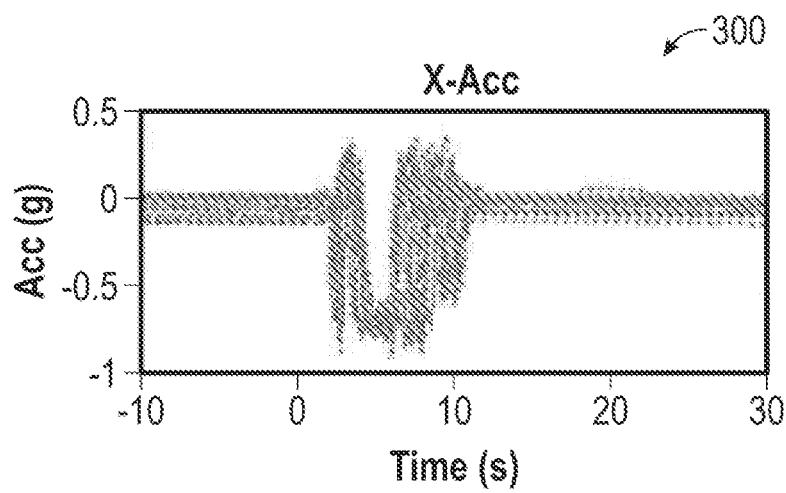
FIG. 3A illustrates exemplary accelerometer data used to detect matter input from the x-axis of the accelerometer.
Figure 3B:
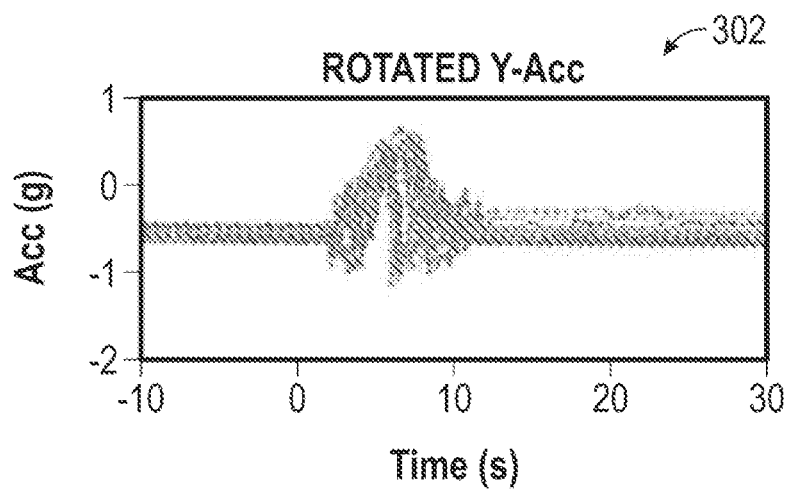
FIG. 3B illustrates exemplary accelerometer data used to detect matter input from the y-axis of the accelerometer.
Figure 3C:
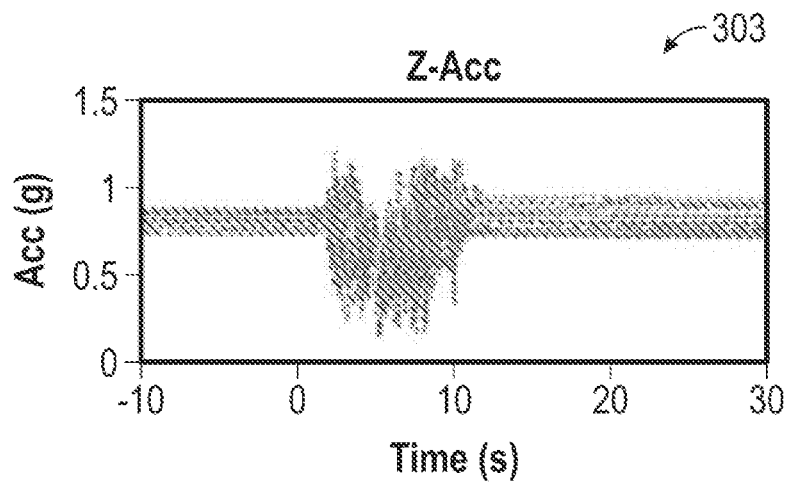
FIG. 3C illustrates exemplary accelerometer data used to detect matter input from the z-axis of the accelerometer.

For example, as shown in FIGS. 3A-3C, the three plots 300, 302, 303 depict the x, y, and z axis of accelerometers, demonstrating that accelerometer data can be used to detect drink events. In the example shown in FIGS. 3A-3C, the acceleration of the wrist of three different subjects was monitored while the subjects ingested twenty different boluses of an electrolyte solution with volumes varying from 0.5 to 4 oz., each, showing a high degree of repeatability from drink motion to drink motion, thus demonstrating that drink motions can be effectively identified using accelerations measured by a wrist-worn motion sensors 133.

Figure 4:
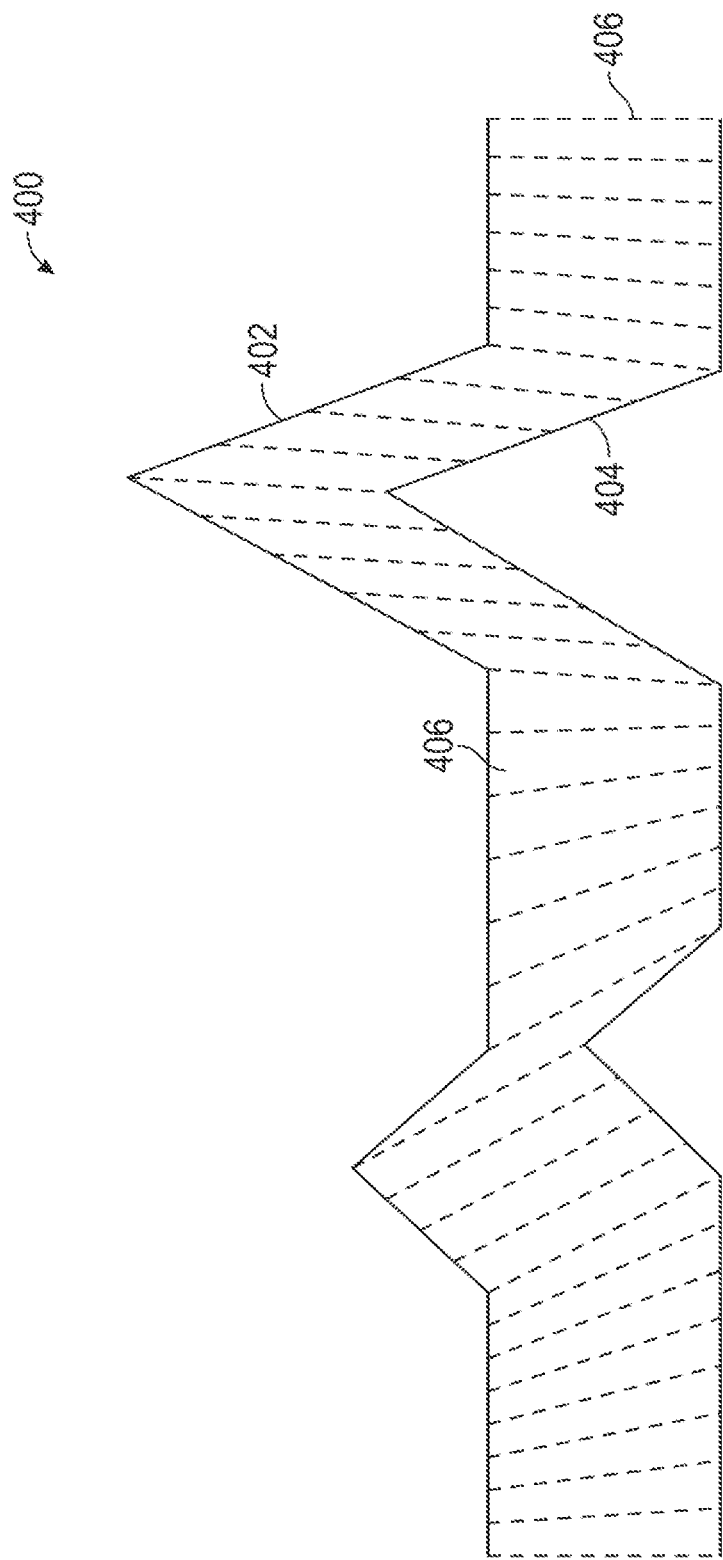
FIG. 4 shows an exemplary diagram of accelerometer data which has been processed by dynamic time warping.

In at least one example, the velocity with which the user's hands move during drinking events can vary considerably from person-to-person and even within the same person. To ensure that drinking motions are represented in a similar way under most conditions, the acceleration data can be segmented and/or pre-processed using techniques such as dynamic time warping, dynamic tiling, and/or fast Fourier transforms after zero padding. FIG. 4 shows an example of dynamic time warping for mapping an input signal 402 into another temporal signal 404 by matching features that are common in both versions of the signal as depicted by dashed lines 406. This common mapping allows the direct comparison of the transformed signal with other signals available in a signal library representative of drinking motions.

Moreover, the motion signals can be processed using adaptive algorithms that are sensitive to temporal variations, such as time-delay and/or finite impulse response (FIR) neural networks, and/or long short term memory networks (LSTMN). Every time a user newly dons a wearable device, the wearable device 122 can be located in a slightly different location. Similarly, different users can drink in slightly different ways. Thus, adaptive signal processing methods can be employed to adjust for user-to-user and/or wear-to-wear variations. For example, a rotation matrix can be used to re-orient the wearable device 122 regardless of the orientation in which the wearable device 122 is worn.

The drink and/or non-drink class of activities can also be distinguished using algorithms such as Normal Activity Recognition, Activity Thresholds, and/or k-nearest neighbors. In Normal Activity Recognition, for example, specific activities can be recognized by first computing the surface normal and then comparing the temporal variation of the surface normal vector against those of pre-trained activities stored in a local library. In the k-nearest neighbors classification method, an input sample point can be assigned the category label of the k nearest set of previously classified points. For example, using a nearest-neighbor algorithm, drinking events can be distinguished from non-drinking events with an accuracy better than 92%, a sensitivity better than 89% and a specificity better than 87%.

Figure 5:
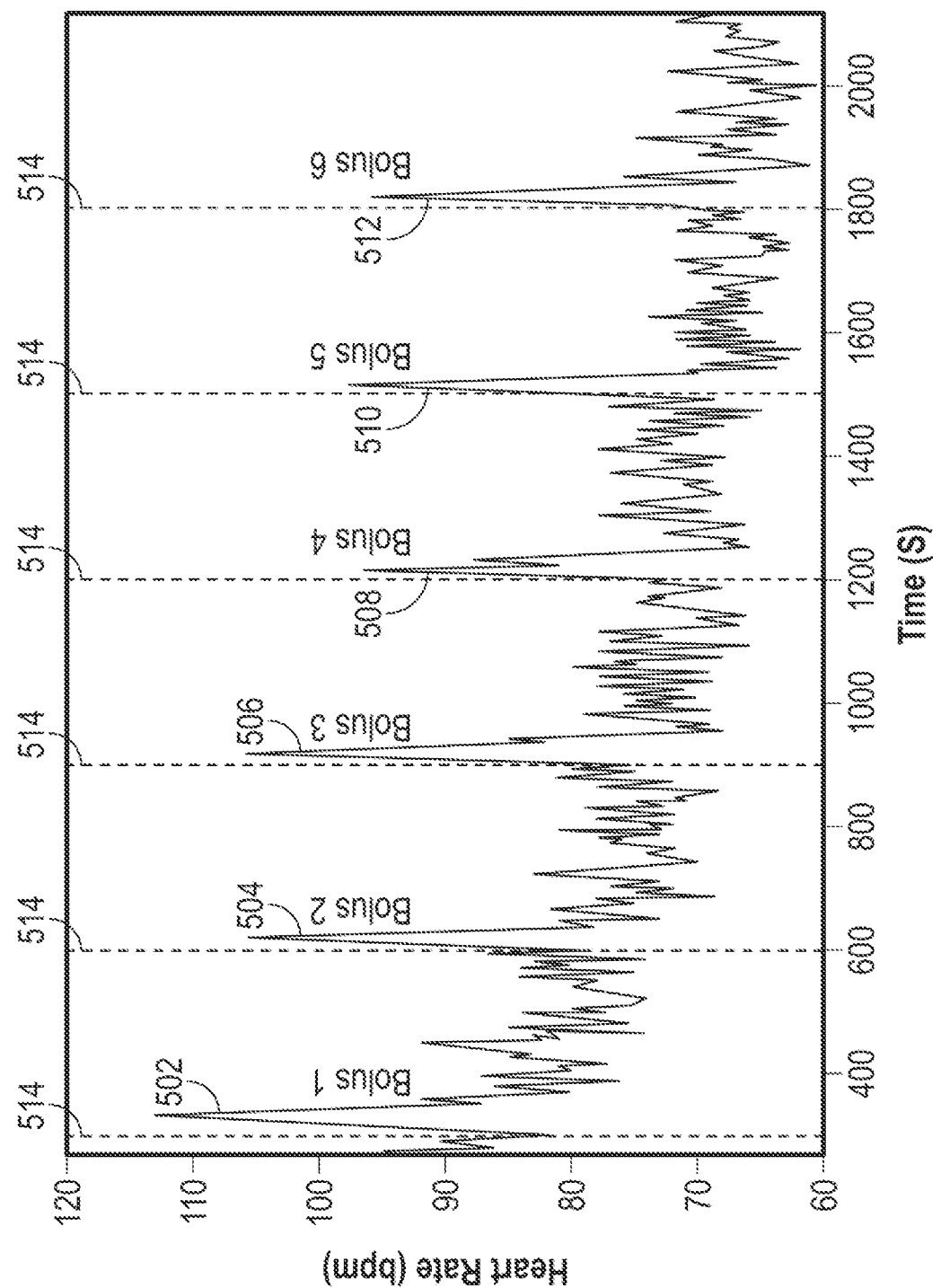
FIG. 5 shows an example using heart rate to detect a drink event.

Referring now to FIG. 5 shows an example of a biological signal used to indicate the time and/or volume of a drink event. In the example shown in FIG. 5, the heart rate of a user was monitored using a heart rate sensor 152 while the user ingested six boluses of an electrolyte solution: 250 ml in the first bolus 502 and 153 ml in each of the subsequent five boluses 504, 506, 508, 510, 512, corresponding to a total of 14 ml per kg of total body mass. The dashed lines 514 mark the beginning of each one of the drink events. The user's heart rate surges shortly after each drink and the surge in heart rate lasts approximately the duration of the drinking event. Therefore, during a drink event both the amplitude and/or duration of the heart rate surge (above baseline) increase as a function of the volume of fluid ingested. In at least one example, the volume of ingested fluid can be estimated by the area-under-the-curve between the surge and/or baseline signals.

Figure 6:
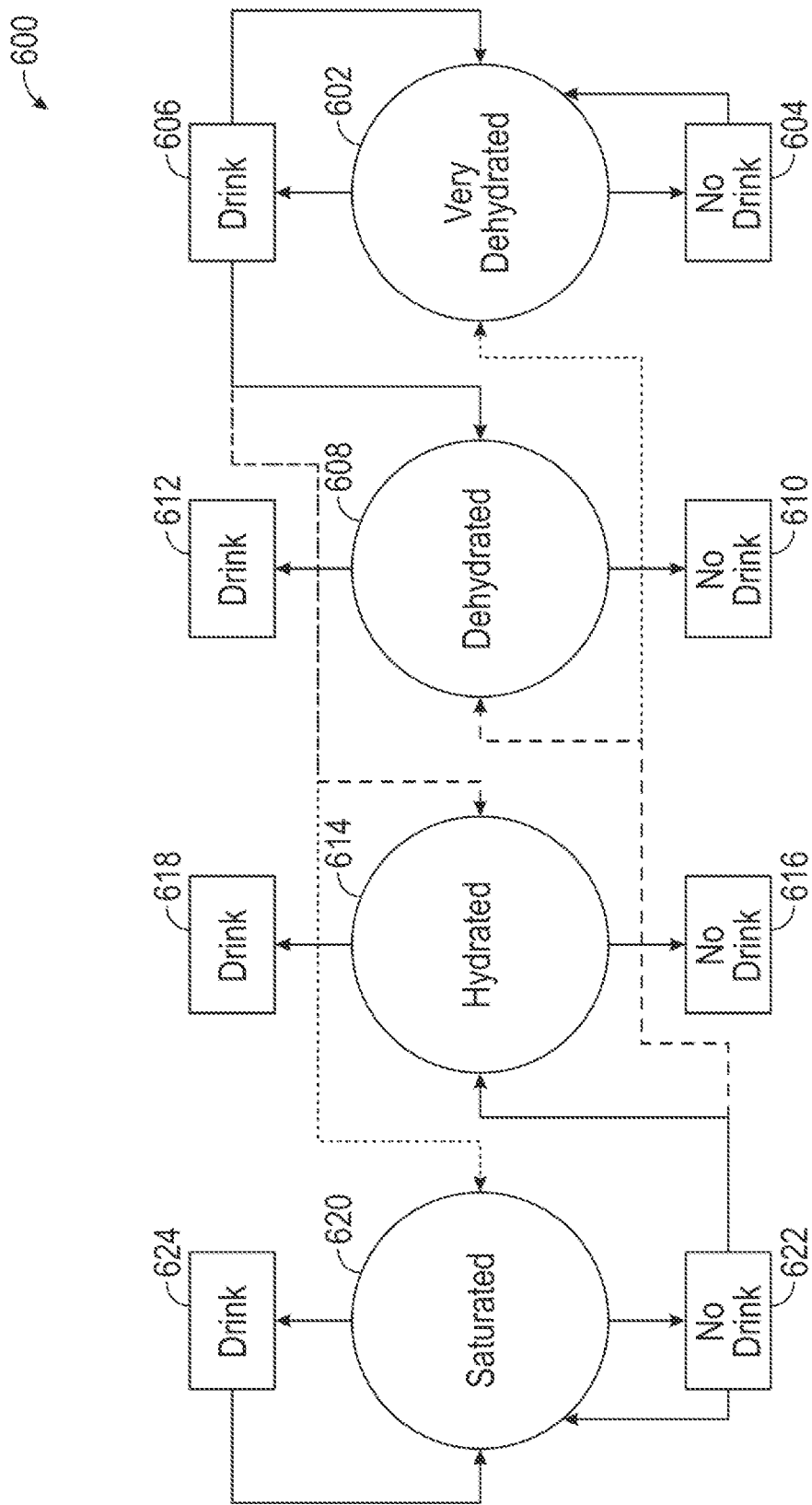
FIG. 6 shows a diagram of drink events corresponding to hydration status.

As shown in FIG. 6, an example of how drink detection events can be used to help determine the hydration status of a user. The diagram 600 shown in FIG. 6 depicts a Markov decision process, where the present state is independent of past states. Methods for solving Markov decision processes include dynamic Bayesian networks and maximum likelihood estimators. Expectation-maximization algorithms, such as the Baldi-Chauvin algorithm and/or the Markov-chain Monte Carlo algorithm, can also be included, as well as on-line learning algorithms such as the Baum-Welch algorithm, the Bayesian online algorithm and/or the Mean Posterior approximation algorithm. Also, the current state of the user can not be known a priori and only inferred from observations of their actions, which is called a "hidden Markov model" and can also be solved by the algorithms listed above, with or without modifications.

In the example diagram 600 shown in FIG. 6, a set of possible user states include saturated 620, hydrated 614, dehydrated 608, and very dehydrated 602 which are represented by circles. Each user state can correlate to a range of hydration levels. For each user state, there are sets of two possible user actions such as drink 624, 618, 612, 606 and no drink 622, 616, 610, 604 which are represented by rectangles. Arrows show possible future states once a user has undertaken a given action, with solid arrows representing transition probabilities that are higher than those of dashed arrows, which are higher than those represented by dotted arrows. For example, when the user state is very dehydrated 602, the user can not drink 604, and the probability of the user being very dehydrated 602 is high. The user can also drink 606, and the probability of the user transitioning to dehydrated 608 or remaining very dehydrated 602 are high. The probability of the user transitioning to hydrated 614 is medium, and the probability of the user transitioning to saturated is low. Note that for exemplary purposes, only the transition probability arrows associated with the Drink action 606 and No Drink action 604 associated with the Very Dehydrated state 602, and the transition probability arrows associated with the Drink action 624 and No Drink action 622 associated with the Saturated state 620 are shown. All other transition probability arrows associated with all actions, all states, do exist but are omitted from diagram 600 for clarity.

The use of at least one sensor 108 and/or biological sensors 124 can be used in isolation or in combination. For example, the mobile device 100 can obtain data from the IMU 134, wherein the determination of one or more drink events is based on the obtained data from the IMU 134 with respect to time and/or heart rate. In at least one example, the time of a heart rate spike and/or motion detected from the IMU 134 can indicate the start of a drink event. Furthermore, predetermined motions, such as a return to a position prior to initiation of the input event, for example, can indicate an end of a drink event.

In at least one example according to the present disclosure, a mobile device 100 is operable to determine habits of a user 208 and to make recommendations regarding changes in habits. The mobile device 100 includes one or more internal sensors 108 operable to detect at least one of a motion of the mobile device 100 and/or location of the device. The mobile device 100 also includes a processor 104 coupled to the one or more internal sensors 108 and/or a display 102 coupled to the processor 104 and operable to display data 314 received from the processor 104. The communication component 118 is coupled to the processor 104 and is operable to receive data 314 from at least one of: a remote computer 168 or one or more external sensor components 122 operable to detect a biological indicator 206. The mobile device 100 further includes a memory 120 coupled to the processor 104 and is operable to store instructions to cause the processor to perform the process of logging input events. In at least one example, the wearable device 122 is operable to determine habits of a user 208 and make recommendations 320 regarding changes in habits without the use of a mobile device 100 and/or a remote computer 168.

In at least one example according to the present disclosure, a mobile device system 200 is operable to provide recommendations on input for a user 208 including one or more of: a mobile device 100 and/or an external sensor 122. The mobile device 100 includes at least one sensor 108 operable to detect motion of the mobile device 100 and/or at least one communication component 118 operable to receive data 314 from one or more external sensor components 122 or remote computer 168. The mobile device 100 also includes a processor 104 coupled to the at least one sensor 108 and/or the at least one communication component 118. The mobile device system 200 also can include one or more of: an external sensor component 122 having a component processor 128; a biological sensor 124 coupled to the component processor 128 and operable to detect a biological indicator 206 of the user 208; and/or a transmitter 126 operable to transmit the detected biological indicator 206 to the at least one communication component 118 of the mobile device 100. The remote computer 168 includes a processor 170 and/or a memory 174 that is operable to store instructions to perform the process of logging input events.

Figure 7:
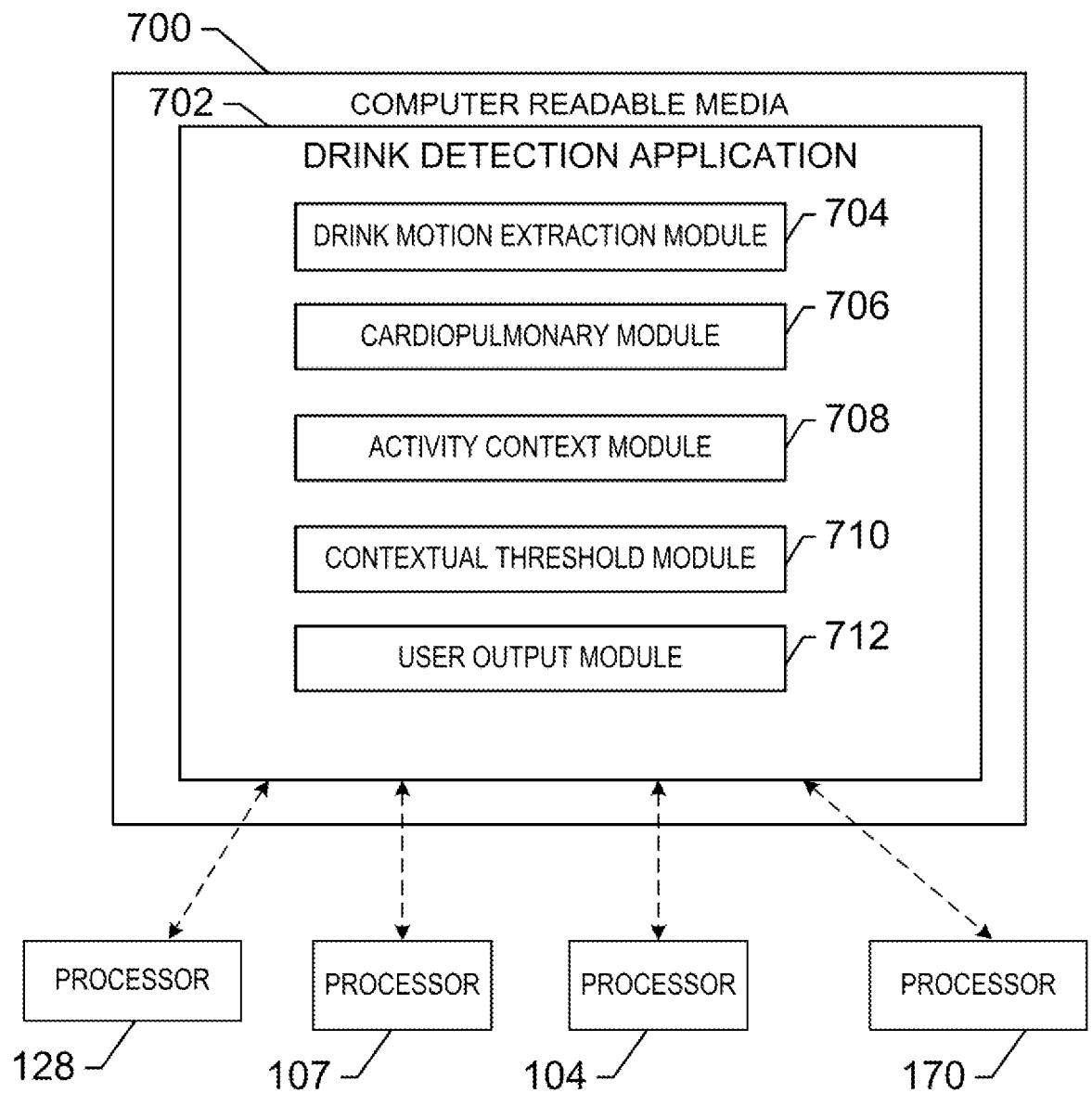
FIG. 7 is a diagram of a drink detection algorithm application, according to the present disclosure.

FIG. 7 illustrates a block diagram of a computer readable media (CRM) 700 that can be read and/or executed by the processors of a computing device, such as the wearable device 122, the mobile deice 100, the remote computer 168, and/or the cloud storage and data processing system 105, according to various embodiments. The CRM 700 can also be stored in memory of the computing devices and can contain the drink detection application 702, other user interface and/or application. The computer readable media can include volatile media, nonvolatile media, removable media, non-removable media, and/or another available medium that can be accessed by the respective processors of the computing devices. By way of example and not limitation, the computer readable media comprises computer storage media and/or communication media. Computer storage media includes non-transitory storage memory, volatile media, nonvolatile media, removable media, and/or non-removable media implemented in a method and/or technology for storage of information, such as computer/machine-readable/executable instructions, data structures, program modules, or other data. Communication media can embody computer/machine-readable/executable instructions, data structures, program modules, or other data and include an information delivery media and/or system, both of which are hardware.

The remote computer 168 can be a laptop computer, a smartphone, a personal digital assistant, a tablet computer, a standard personal computer, and/or another processing device. The remote computer 168 can include a display 177, such as a computer monitor, for displaying data and/or graphical user interfaces. Each computing devices 122, 100, 168, and/or 105, can also include an input device 179, such as a camera, a keyboard and/or a pointing device (e.g., a mouse, trackball, pen, and/or touch screen) to enter data into and/or interact with graphical and/or other types of user interfaces. In an exemplary embodiment, the display 177 and/or the input device 179 can be incorporated together as a touch screen of the smartphone and/or tablet computer.

Furthermore, the at least wearable device 122 can display on the display 177 a graphical user interface (or GUI) application to generate a graphical user interface on the display. The graphical user interface can be generated by one or more modules of the drink detection application 702. The graphical user interface enables a user of the at least one mobile device 100 and/or user-worn device 122 to interact with the drink detection application 702.

The drink detection application 702 can be a component of an application and/or service executable by the at least one client computing device 104 and/or the motor carrier computing device 105 and/or the at least one server computing device 102. For example, the drink detection application 702 can be a single unit of deployable executable code and/or a plurality of units of deployable executable code. According to one aspect, the drink detection application 702 can include one component that can be a web application, a native application, and/or a mobile application (e.g., an app) downloaded from a digital distribution application platform that allows users to browse and/or download applications developed with mobile software development kits (SDKs) including the App Store and/or GOOGLE PLAY®, among others.

As shown in FIG. 7, the drink detection application 702 can include a number of modules executable by at least one of the processors 104, 107, 128, and/or 170 of at least one of the mobile device 104, wearable device 107, and/or the remote computing device 168. The modules include but are not limited to a drink motion extraction module 704, a cardiopulmonary module 706, an activity context module 708, a contextual threshold module 710, and/or a user output module 712. Although identified as individual modules for the purposes of illustration, the functionality of the modules 704-712 can be combined and/or overlap with the functionality of other modules. In addition, the modules 704-712 can be located on a single CRM 214 and/or distributed across multiple computer readable media on multiple computing devices.

In various aspects, the modules 704-712 can reside and/or be executed at one or more computing device of the system 200. For example, in one embodiment, all data processing and/or analysis takes place on the wearable device 122.

In another example, the majority but not all data processing and/or analysis takes place on the wearable 122 device. In this example, processing and/or analysis for a small sample set (e.g. only the most recent data measures ~1000 data measurements or less) is performed on the wearable device. Analysis of larger data sets can be performed at more robust computing devices. As such, the wearable device 122 requires limited memory and/or processing capabilities.

In yet another example, little to no processing takes place on the wearable device 122. The data captured by the sensors 132 and/or 134 on the wearable device 122 is streamed to the mobile device 100. In various aspects, the data processing and/or analysis occurs on the mobile device 100, the remote computer 168, and/or at the cloud processing system 105.

The drink motion extraction module 704 receives and/or processes motion data captured by one or more accelerometers of the sensors 132. Suspected drink motions are identified from the drink motion data by dynamic time warping. In particular, the drink motion extraction module 704 uses machine learning techniques. In one aspect, the module 704 is trained using data including known drinking and/or sucking motions, known motions often confused with drinking motions, (e.g. combing hair, opening doors with vertical handles), and/or known non-drinking motions.

The motion detection algorithms are combinations of dynamic time warping (DTW) algorithms and/or time-series versions of classification algorithms. These can include but are not limited to linear discriminant analysis (LDA), quadratic discriminant analysis (QDA), and/or a support vector machine (SVM). The drink motion extraction module 704 generates specialized signals for subsequent analysis at the contextual threshold module 710.

To determine that a drink event occurred with greater accuracy, the wearable device 122 can correlate biological indicators from biological sensors 124 along with the motion signals from the motion sensors 133. As such, the drink detection application 702 also includes cardiopulmonary module 706 that receives cardiopulmonary data such as a heart rate (HR), cardio-inter-beat intervals (IBI), breathing rate (BR) and pulmonary-inter-breath interval (ibi), and/or other dynamic pulmonary movements, such as a cough and/or sneeze. In various aspects, the data signals are derived from time-frequency analysis of PPG data and IMU data.

The cardiopulmonary module 706 generates signals to highlight known swallowing and sucking signals that can be derived from the heart rate and breathing. The events identified also include swallowing and/or sip motions, straw sucking, and chugging motions that change the respiratory motions of the system user.

As readily understood, the respiration rate of the user undergoes periodic inhale/exhale cycles. Thus, drinking events that interrupt these cycles can be identified by the cardiopulmonary module 706. In one aspect, the cardiopulmonary module 706 generates Poincare plots illustrating heart rate variability that can detect abnormalities in the cardiac cycle and/or the breathing cycle. In particular, while cardiac (HRV) Poincare' plots only take into account RR intervals, breathing cycles also include exhales, requiring three dimensions to represent a complete cycle in a Poincare' plot, along the dimensions of $ibi^{t-1}_{insp}$, $ibi^{t}_{exp}$, and $ibi^{t}_{insp}$.

For example, a user stops breathing in order to take a drink. As such, the biological indicator can include a breathing rate, and/or pauses in breathing. Additionally, to compensate for the momentary loss in arterial blood oxygenation due to the user stopping breathing, the user's circulatory system increases oxygen delivery by increasing the blood flow and/or by increasing the heart rate. As such, the heart rate variability (HRV) also increases while the user respiration rate suffers a decrease. Therefore, the biological indicator can include a surge in heart rate and/or changes in HRV.

Drinking may not be the only action that causes a change in heart rate over a period of time. The period of time can be, for example, 3 seconds, 10 seconds, or 30 seconds. Changes in heart rate can also be caused by other actions that require compensation through a change in blood volume. For example, when a person stands up suddenly their heart rate usually increases to assure proper oxygenation to their head at a higher elevation. As such, the wearable device 122 can utilize additional biological indicators indicative of a drink event. For example, the thermometer component 144 can provide biological indicators that can include changes in skin and/or core temperatures, changes in skin and/or core temperatures with respect to ambient temperature as drinks tend to be at a different temperature compared to ambient temperature. For example, drinks tend to be cold when the ambient temperature is hot and vice-versa. Another biological indicator can be an increase in skin perfusion. The skin typically works as a water reservoir. As such, when a user dehydrates, their peripheral vasculature can constrict, leading to reduced perfusion in the skin and/or extremities. Conversely, when a user drinks and/or rehydrates, perfusion can increase. As such, a near-infrared spectrometer 146 can measure tissue hydration and/or tissue perfusion, and the wearable device 122 can determine that a drink event is detected when an increase in tissue perfusion is measured. Other examples of biological indicators that can be used to detect drink events include the sounds and/or images associated with drinking, which can be captured by microphones, still and/or video cameras embedded on the wearable device 122 and/or the mobile device 100.

Drinking also can increase the amount of blood plasma and the balance between intracellular and extracellular fluids, and that change in ratio, such as tissue hydration variation, can be measured using bioimpedance monitors 148. During water absorption events, water is typically first ingested orally before being absorbed by the digestive tract, at which point the water is transferred into the blood plasma. From the blood plasma, water is distributed throughout the body to arterioles and/or capillaries, where water becomes extracellular fluid before being osmotically absorbed by the cells in the body, thus becoming intracellular fluid. Cell membranes contain fatty tissue and are thus highly resistant to electric current while fluid is highly conductive. Thus, measuring the bioimpedance of the body provides one with an estimate of the ratio of intracellular over extracellular fluid content, thereby providing us with an estimate of fluid flow within the user body. The bioimpedance monitors 148 can measure biological indicators including galvanic skin response, skin resistance, skin conductance, electrodermal response, psychogalvanic reflex, skin conductance response, sympathetic skin response, skin conductance level, and/or electrodermal activity.

The drink detection application 702 also includes an activity context module 708 that receives data/signals from the both the motion sensors 133 and/or physiological signals from the biological sensors 124. In one aspect, the activity context module 708 processes the received data to further determine the conditions under which the measurements were made. For example, when the user is sleeping, it is less likely that a drink will be had. Conversely, during a period of exercise, there is an increased likelihood of detecting a drinking motion. In other aspects, the activity context module 708 uses the received data measurements to determine when the user is likely sitting, walking, or exercising, riding in a car among others. In another aspect, the activity context module can access a consensus set of patterns built from a large number of subjects in relevant demographic populations and/or geographic locations. Similarly, the contextual data can be adaptive and/or personalized for the user. For example, the types and/or context of drinks could be personalized, such as indicating when a user always drinks from a straw or only drinks while seated around mealtimes.

The drink detection application 702 also includes a contextual threshold module 710 varies a threshold for confirming or rejecting a suspecting drinking motion based on the outputs of the drink motion extraction module 704, the cardiopulmonary module 706, and/or the activity context module 708.

In one aspect, motion, heart rate, and/or breathing rate measurements and/or changes in the measurements can independently signal the presence of a drink. For example, if the device is not worn on the hand that is drinking we expect to see HR/BR modulations without motion. Similarly, if other physiological events are taking place during a drink we can see motion without a strong HR/BR modulation. So each of these methodologies has a threshold associated with it (i.e. motion threshold ($T_m$) and HR/BR threshold ($T_o$)).

In various aspects, the thresholds can be contextually adapted and/or varied to better account for the likelihood that a drink motion is to occur. For example, if drinks have recently been detected, then the drink detection threshold can be lowered, thus increasing the probability that a temporally proximate drink motion is classified as an actual drink motion. Conversely, the thresholds during periods of sleep are made very high, thus decreasing the likelihood that a potential drink motion is classified as an actual drink motion.

As described, contextual clues and/or user activity can modulate the threshold level based on the quality of the gathered measurements and/or the probability of drinking during each activity. For example, the measurements can be more precise and/or of higher quality when the user is sitting. Alternatively, the measurements can be less accurate and/or lower quality when the user is exercising. The thresholds can be further modulated or set based upon cross modality confirmation. For example, cross modality confirmation refers to the combined use of thresholds for both motion-based detection and cardiopulmonary based detection to accept or tally drinks that can otherwise be rejected when compared with a motion threshold or cardiopulmonary threshold, individually. In one aspect, cross modality confirmation can lead to the acceptance or tallying of drinks that do not meet the threshold criterion for motion-based detection and do not meet the threshold for cardiopulmonary based detection. In this aspect, the motion-based detection threshold can be reduced when the cardiopulmonary based detection threshold is in a region around, but still lower than the motion-based threshold. Similarly the cardiopulmonary threshold may be reduced based on its proximity to the motion-based threshold.

In addition to detecting drinking events, the drink detection application 702 can be further configured to estimate a volume of liquid ingested with each drink. According to one aspect the volume of each sip, chug, and/or drink can be estimated using the motion dynamics of the drink as well as the cardiopulmonary characteristics. The number of drinks and/or the total estimated volume can both be stored and/or presented to users.

Additionally, to improve the detection of drink events, the wearable device 122 and/or the mobile device 100 can access specific events on the user's calendar and/or social media accounts to aid in the determination of whether or not the user is undergoing a drink event at a given time. For example, references to words such as "Lunch," "Dinner," and "Breakfast" are associated with a higher probability of drinking while words such as "Run," "Workout," and "Spin class" are more closely associated with output events that lead to a loss of hydration volume due to increased physical activity, resulting in a higher loss of liquids due to increased perspiration and/or respiration rate. The wearable device 122 and/or the mobile device 100 can also use one or more of the user's contacts and/or calendar events to determine whether the user is in a location and/or the presence of one or more people with whom the user experiences drink events.

Additionally, the wearable device 122 and/or the mobile device 100 can use the user's physical location to assist in the estimate of whether the user is likely to undergo an input or output event. For example, the probability of the user drinking is higher when the user is in a restaurant, bar, cafe, and/or cafeteria. Indicators of physical location can also include ambient light and/or UV exposure detectors measured, for example, by ambient light sensors 154, indicating whether the user is indoors or outdoors. Additional examples of physical location indicators can include knowledge of previous locations regularly visited by the user and stored in memory 186, the use of altitude sensors 158, atmospheric pressure sensors 156, and/or relative humidity sensors 160 detectors to determine whether the user is indoors or outdoors and/or at what floor of a given building, and captured images and/or videos by camera 184. The wearable device 122 and/or the mobile device 100 can also send one or more notifications 133 to the user 208. The notifications 133 can also be provided to the user 208 via one or more of a display, lights, sound, vibrations, and/or buzzers.

Figure 8:
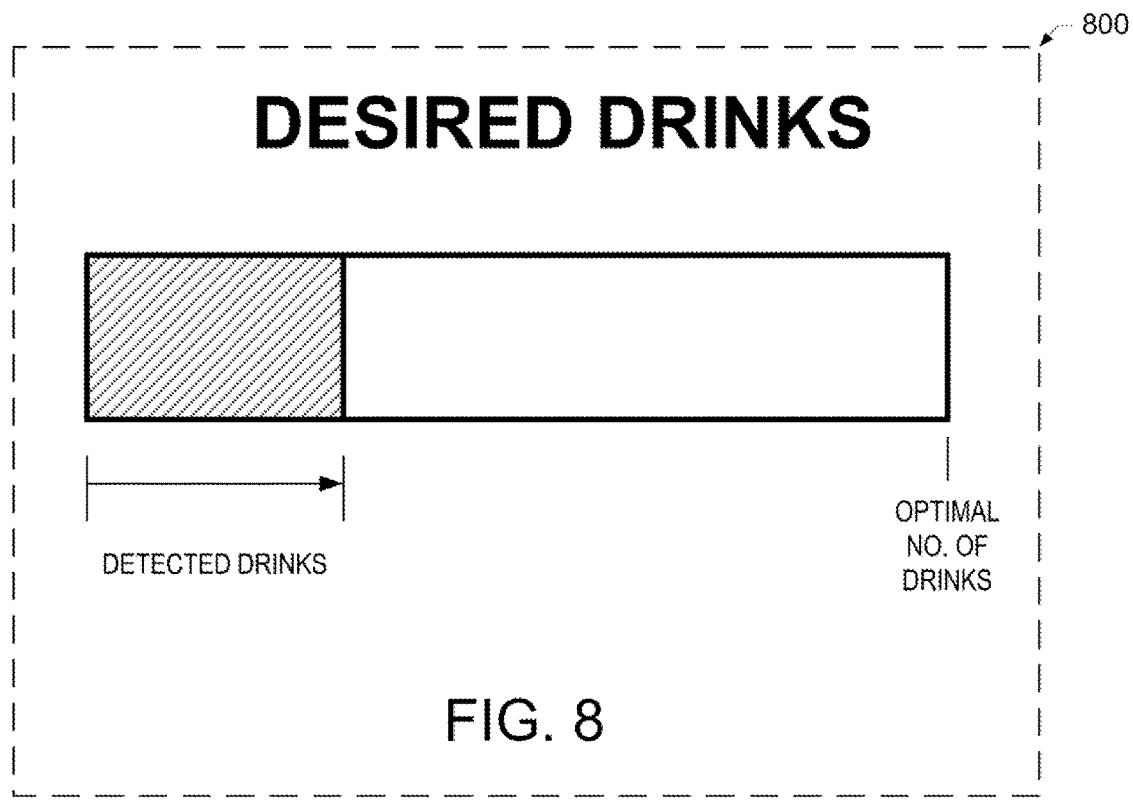
FIG. 8 is one example of a displayed drink monitoring graphic according to the present disclosure.

The drink detection application 702 also includes a user output module 712. The user output module 712 can provide an indication to the user that a drink should be taken. The output module 712 can also generate a display, such as one embodiment of a display 800 as shown in FIG. 8. As shown, the display 800 includes a graph and/or chart to shown the number of drinks taken relative to an optimal number of drinks. In other aspects, the graph could be linear, curved (like a ring), and/or some other representation. By way of example, the graph can include display a plurality of drinking glasses, a large vessel of water that is filled in relation to drinks taken, and/or a plant that grows and/or straightens up as the user drinks. In one aspect, the total scale could be representative of the total number of drinks and/or a desired total volume of liquid and each drink could fill in a portion of the graph.

Figure 9:
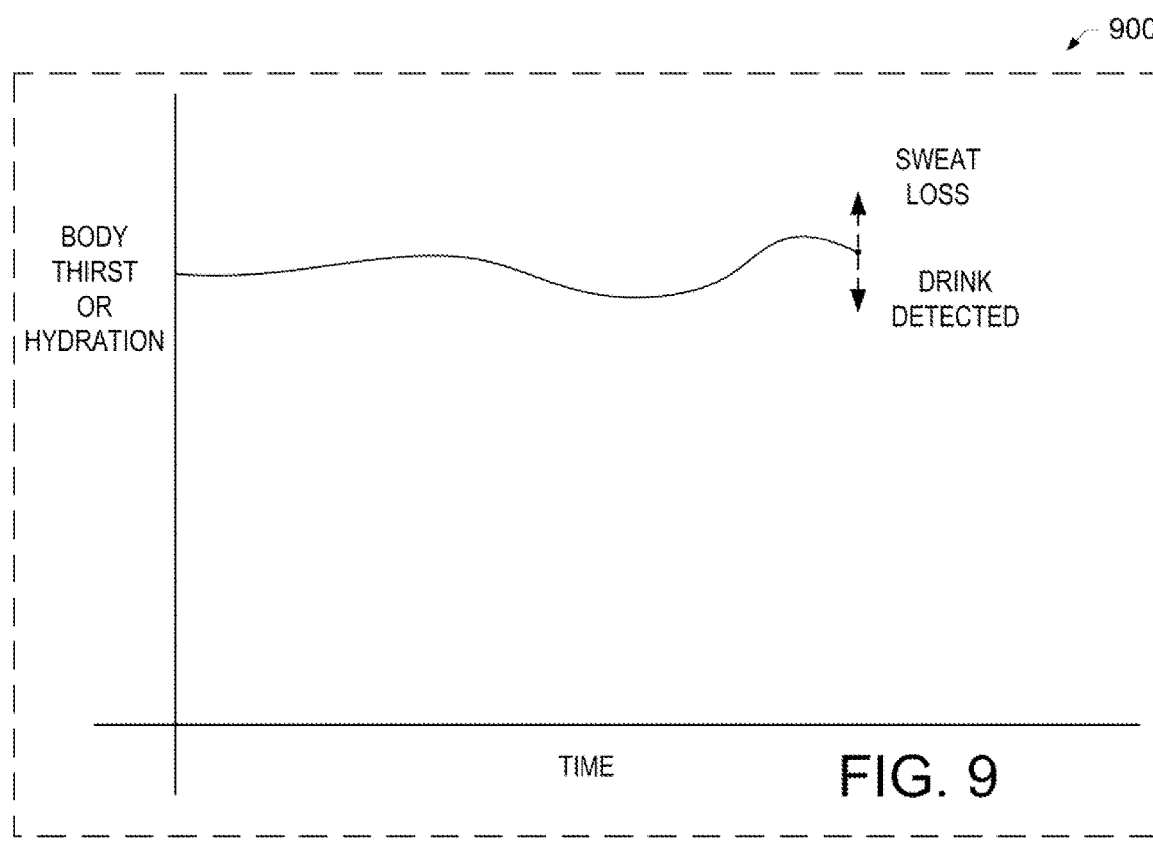
FIG. 9 is one example of a displayed drink monitoring graphic according to the present disclosure.

Another embodiment of a display 900 that can be generated by the user output module 712 is shown in FIG. 9. In this display, the historical hydration and/or thirst levels of the user as a function of time can be shown. As indicated, the hydration and/or thirst level of the user varies over time. The hydration and/or thirst level can decrease based upon fluid lost during sweat and alternatively can increase in response to the drinks taken by the user.

In other aspects, user output module 712 can meter the displayed output such that allow one drink and/or some predetermined volume of liquid drank per unit of time is displayed in order to encourage the user of the system to take time between drinks. Similarly, the user output module 712 can provide direct feedback of drinking events and/or hydration levels. For example, the user output module 712 can initiate a vibration notification, audible tone, and/or an illuminated signal on the wearable device 122 and/or the mobile device 100 when a goal volume for the hour, day, week, or other period is met.

In one aspect, the user output module 712 is adapted to log or record and/or indicate the time and/or volume of each drink. The output module 712 can further receive input from the user to edit the drink log by adding or rejecting tallied drinks and/or to adjust the calculated volume of liquid drank by the user.

Figure 10:
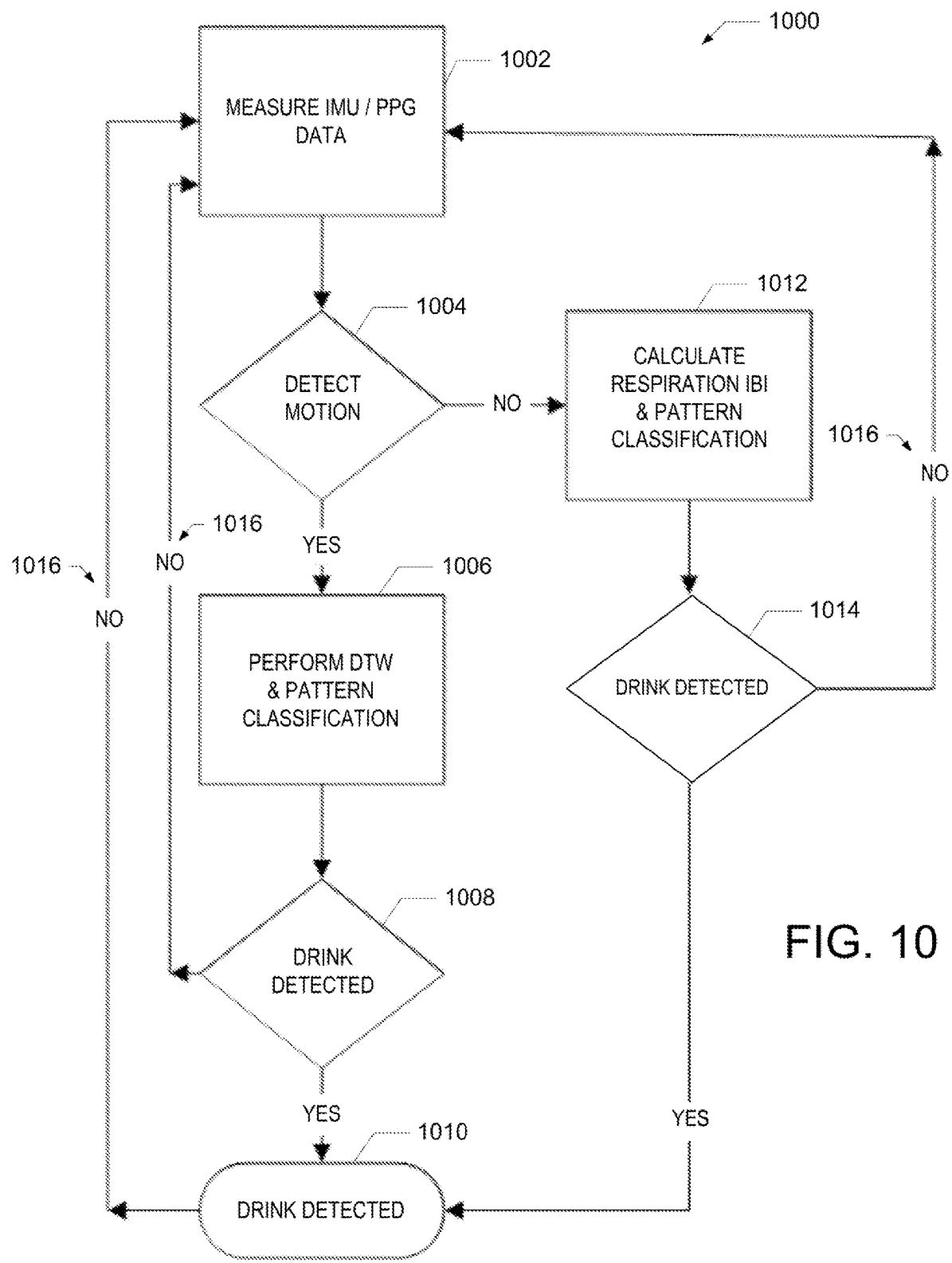
FIG. 10 is flowchart illustrating a method or process for contextual drink detection according to the present disclosure.

FIG. 10 illustrates a block diagram detailing a method of drink detection using from motion and/or optical sensors according to at least one instance of the present inventive concept. Method 1000 can use various machine-learning based pattern classification processes to distinguish between physical drinking motions and a drink respiration pattern, both of which may be identified as drinks. As shown, the method 1000 is described and implemented with respect to the systems, devices, and applications as described with respect to FIGS. 1-9. While the method 1000 is shown and described with respect to blocks 1002-1016, it is within the scope of this disclosure to implement any number of blocks, including omission of one or more blocks of method 1000 or inclusion of additional blocks not specifically described with respect to method 1000. Further, while blocks are described sequentially, no specific order is implied nor required. Method 1000 can begin at block 1002.

According to one aspect, at block 1002, motion data and/or cardiopulmonary data are captured by sensors, such as 133 and/or 124. At block 1004, a determination is made at the drink motion extraction module 704, to determine if an actual user motion is detected based on the captured motion data. If the determination is affirmative, then further analysis is performed by the drink motion extraction module at block 1006 to determine if the identified motion is a drink motion at block 1008. If the motion is identified as a drink motion at block 1008, then a drink is detected and reported to the user at block 1010. As indicated by 1016, whether or not a motion is detected, the method returns to block 1002 to continuously monitor the sensors 133 and/or 124.

Referring now back to block 1004, if the no clear motion is detected at the drink motion extraction module 704, the data is further processed at the cardiopulmonary module 706 at block 1012. At the cardiopulmonary module, a respiration inter-breath-interval (IBI) is calculated and used in a machine-learning based pattern classification analysis to determine if the pattern is a drink as block 1014. If the pattern is not identified as a drink, the method returns, as indicated by 1016, to block 1002 where the motion and/or optical sensors a continuously collecting motion and/or cardiopulmonary data. Conversely, if the motion is identified as a drink, then a drink is tallied and reported to the user at block 1010.

In various embodiments, the drink detection determinations performed at block 1008 and/or block 1014 further includes contextual data also gathered by the sensors 133 and/or 124. In particular, the contextual data is processed at the activity context module 708 and/or the contextual threshold module 710 to generate or modify a contextual threshold that can be used to aid in the detection of an actual drinking motion.

Figure 11:
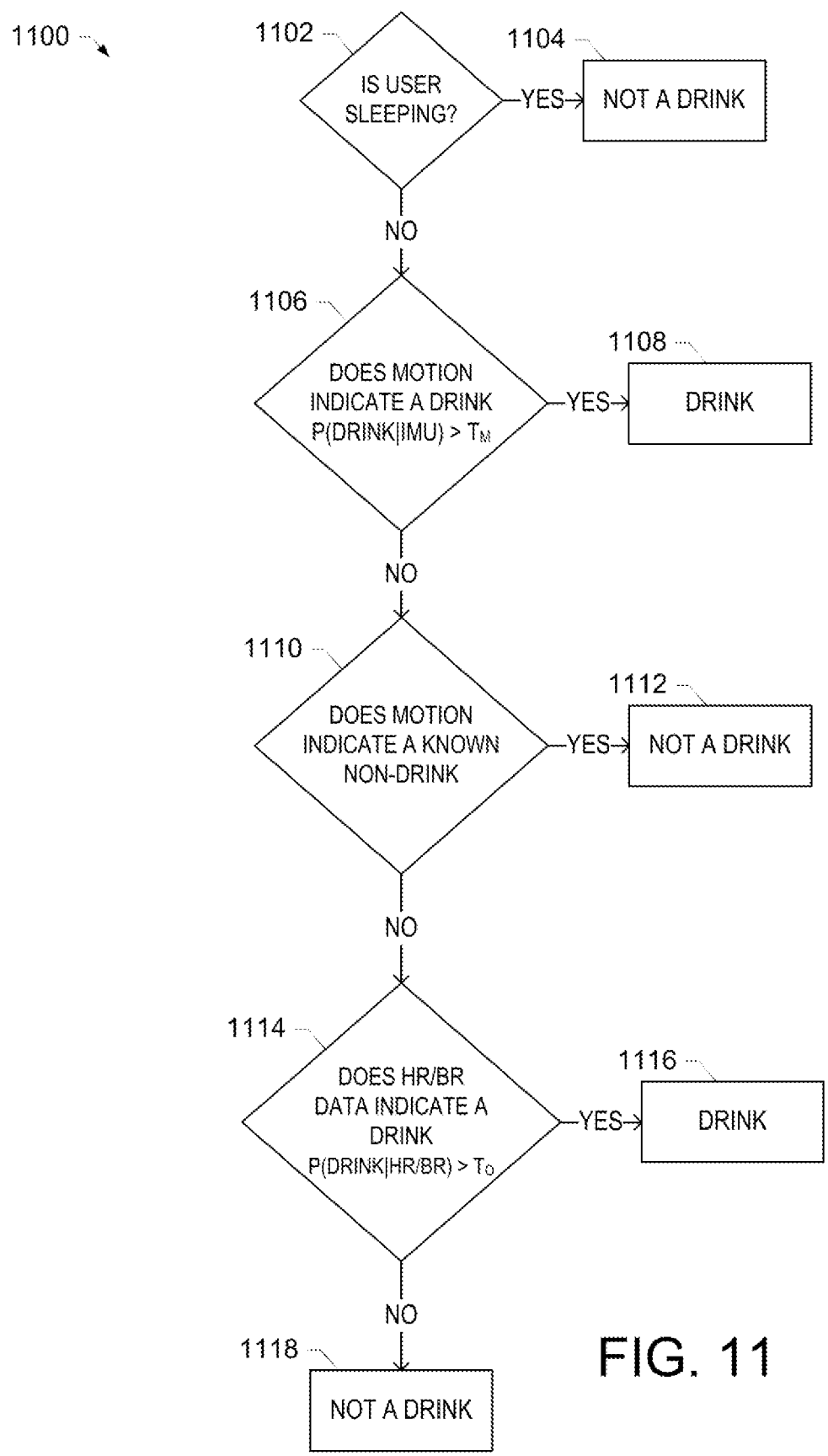
FIG. 11 is flowchart illustrating a sub-process of in-context drink detection according to the present disclosure.

FIG. 11 illustrates a block diagram detailing a method for in context drink detection according to at least one instance of the present inventive concept. Method 1100 is described and implemented with respect to the systems, devices, and applications as descried with respect to FIGS. 1-10. In one aspect, the method 1100 is performed by the execution of the contextual threshold module 710 of FIG. 7, at a processor. While the method 1100 is shown and described with respect to blocks 1102-1118, it is within the scope of this disclosure to implement any number of blocks, including omission of one or more blocks of method 1100 or inclusion of additional blocks not specifically described with respect to method 1100. Further, while blocks are described sequentially, no specific order is implied nor required. Method 1100 can begin at block 1102.

At block 1102, a first determination is made whether the system user is asleep. If the output of the activity context module 708 indicates that the user is sleeping, the contextual threshold module 710 increases the threshold such that a majority of motions are classified as non-drink motions at block 1104. Conversely, if the activity context module 708 indicates that the user is not sleeping, at block 1106 the contextual threshold module 710 processes the input data against a motion threshold ($T_m$) by the function: $P(Drink|IMU) > T_m$. As previously noted, the threshold $T_m$ varies and can be raised or lowered depending on the output of the activity context module 708. In various aspects, baseline thresholds are derived from population and/or demographic based models compiled from previously collected data. In various aspects, the data can also be gathered from previous user data and/or data from other users most like the current user.

If the determined motion is greater than $T_m$ then a drink is tallied at block 1108. Conversely, if the motion is less than $T_m$, then the method proceeds to block 1110, where the motion is further analyzed to determine if the received data correlates to a known non-drink motion. If the motion correlates to a non-drink motion, then the received data is classified as a non-drink at block 1112. However, if the received data does not correlate to a known non-drink motion, then the process proceeds to block 1114, where the contextual threshold module 710 also processes data related to cardiopulmonary function. In particular, the contextual threshold module 710 further processes the cardiopulmonary data against a HR/BR threshold ($T_o$) by the function: $P(Drink|HR/BR) > T_o$. As previously noted, the threshold $T_o$ varies and can be raised or lowered depending on the output of the activity context module 708. Using the received motion data, cardiopulmonary data, and/or activity context data from the activity context module 708, the contextual threshold module 710 makes a final drink or non-drink determination as indicated by block 1116 and block 1118, respectively, which are stored in a database and/or cloud storage 214 and can be provided to the user.

Numerous examples are provided herein to enhance understanding of the present disclosure. A specific set of statements are provided as follows.

Statement 1: A system for contextual drink detection for a user wearing one or more body-worn sensors, the system comprising: a memory; and at least one processor to: receive data from the one or more body-worn sensors; determine if the received data includes motion data or biological data; wherein when the received data includes motion data, the processor to: classify the motion data as a pre-determined motion pattern; determine if the classified pre-determined motion pattern corresponds to a drink; wherein when the classified pre-determined motion pattern is identified as the drink, the processor to tally the drink, transmit a notification to a computing device of a user wearing the body-worn sensors, and poll the body-worn sensors for additional data; and wherein when the classified pre-determined motion pattern is not identified as the drink, the processor to poll the body-worn sensors for the additional data; and wherein when the received data includes biological data, the processor to: determine at least one of a respiration rate, heart rate, or heart rate variability of the user; determine if the at least one respiration rate, heart rate, or heart rate variability of the user corresponds to the drink; wherein when the at least one respiration rate, heart rate, or heart rate variability of the user corresponds to the drink, the processor to tally the drink, transmit a notification to a computing device of a user wearing the body-worn sensors, and poll the body-worn sensors for the additional data; and wherein when the at least one respiration rate, heart rate, or heart rate variability of the user does not correspond to the drink, the processor to poll the body-worn sensors for the additional data.

Statement 2: The system according to Statement 1, wherein the determination of the drink motion is informed by contextual data and system further comprising: the processor to: receive contextual data; generate a variable contextual threshold based on the contextual data; wherein the received data is more likely to be identified as the drink motion when the contextual threshold is lower than a baseline value; and wherein the received data is less likely to be identified as the drink motion when the contextual threshold is greater than a baseline value.

Statement 3: The system according to Statement 2, further comprising: the processor to: determine if the user of the body-worn sensors is sleeping; and determine if the motion data corresponds to a known non-drink motion.

Statement 4: The system of any one according to Statements 1-3, wherein the motion data is pre-processed using dynamic time warping.

Statement 5: The system according to Statement 1, wherein the one or more body-worn sensors comprises at least one motion sensor and one or more biological sensors.

Statement 6: The system according to Statement 5, wherein the at least one motion sensor includes at least one of an inertial motion unit, an accelerometer, a magnetometer, and a gyroscope.

Statement 7: The system according to Statement 5, wherein the one or more biological sensors includes a photoplethysmography monitor, and the biological data comprises at least one of blood oxygen saturation data, heart rate data, heart rate variation data, blood pressure data, and respiration rate data.

Statement 8: The system of any one according to Statements 1-7, wherein at least one of the motion data and the biological data is processed by a machine learning classification technique.

Statement 9: The system of any one according to Statements 1-7, wherein the transmitted notification to the user comprises a graphic display.

Statement 10: The system according to Statement 9, wherein the graphic display indicates a number of drinks taken by the user.

Statement 11: The system according to Statement 9, wherein the graphic display indicates the user hydration level over time.

Statement 12: The system according to Statement 1, wherein motion data, biological data, or both motion data and biological data are used to identify the drink.

Statement 13: A method for contextual drink detection of a user wearing one or more body-worn sensors; the method comprising: receiving, by at least one processor, data from the one or more body-worn sensors; determining, by the at least one processor, if the received data includes motion data or biological data; wherein when the received data includes motion data: classifying, by at least one processor, the motion data as a pre-determined motion pattern; determining, by the at least one processor, if the classified pre-determined motion pattern corresponds to a drink; wherein when the classified pre-determined motion pattern is identified as the drink by the at least one processor, tallying the drink, transmitting a notification to a computing device of a user wearing the body-worn sensors, and polling the body-worn sensors for additional data; and wherein the classified pre-determined motion pattern is not identified as the drink by the at least one processor, polling the body-worn sensors for the additional data; and wherein when the received data includes biological data: determining, by the at least one processor, at least one of a respiration rate, heart rate, or heart rate variability of the user; determining, by the at least one processor, if the at least one of a respiration rate, heart rate, or heart rate variability corresponds to the drink motion; wherein when the at least one respiration rate, heart rate, or heart rate variability of the user is determined to correspond to the drink by the at least one processor, tallying the drink, transmitting a notification to a computing device of a user wearing the body-worn sensors, and polling the body-worn sensors for the additional data; and wherein when the at least one respiration rate, heart rate, or heart rate variability of the user is determined not to correspond to the drink by the at least one processor, polling the body-worn sensors for the additional data.

Statement 14: The method according to Statement 13, wherein the determination of the drink motion is informed by contextual data; method further comprising: receiving, by the at least one processor, contextual data; generating, by the at least one processor, a variable contextual threshold based on the contextual data; identifying, by the at least one processor, the received data as the drink motion when the contextual threshold is lower than a baseline value; and identifying, by the at least one processor, the received data as a non-drink motion when the contextual threshold is greater than a baseline value.

Statement 15: The method according to Statement 14, further comprising: determining, by the at least one processor, if the user of the body-worn sensors is sleeping; and determining, by the at least one processor, if the motion data corresponds to a known non-drink motion.

Statement 16: The method of any one according to Statements 13-15, further comprising pre-processing, by the at least one processor, the motion data using dynamic time warping.

Statement 17: The method according to Statement 13, wherein the one or more body-worn sensors comprises at least one motion sensor and one or more biological sensors.

Statement 18: The method according to Statement 17, wherein the at least one motion sensor includes at least one of an inertial motion unit, an accelerometer, a magnetometer, and a gyroscope.

Statement 19: The method according to Statement 17, wherein the one or more biological sensors includes a photoplethysmography monitor, and the biological data comprises at least one of blood oxygen saturation data, heart rate data, heart rate variation data, blood pressure data, and respiration rate data.

Statement 20: The method of any one according to Statements 13-19, further comprising processing, by the at least one processor, at least one of the motion data and the biological data using a machine learning classification technique.

Statement 21: The method of any one according to Statements 13-19, wherein the transmitted notification to the user comprises generating, by the at least one processor, a graphic display.

Statement 22: The method according to Statement 21, wherein the graphic display indicates a number of drinks taken by the user.

Statement 23: The method according to Statement 21, wherein the graphic display indicates the user hydration level over time.

Statement 24: The method according to Statement 13, wherein motion data, biological data, or both motion data and biological data are used to identify the drink.

Statement 25: A non-transitory computer-readable storage medium, having instructions for contextual drink detection stored thereon that, when executed by a computing device cause the computing device to perform operations, the operations comprising: receiving data from the one or more body-worn sensors; determining if the received data includes motion data or biological data; wherein when the received data includes motion data: classifying the motion data as a pre-determined motion pattern; determining if the classified pre-determined motion pattern corresponds to a drink; wherein the classified pre-determined motion pattern is identified as the drink by the at least one processor, tallying the drink, transmitting a notification to a computing device of a user wearing the body-worn sensors, and polling the body-worn sensors for additional data; and wherein when the classified pre-determined motion pattern is not identified as the drink by the at least one processor, polling the body-worn sensors for the additional data; and wherein when the received data includes biological data: determining at least one of a respiration rate, heart rate, or heart rate variability of the user; determining if the at least one of a respiration rate, heart rate, or heart rate variability corresponds to the drink motion; wherein when the at least one respiration rate, heart rate, or heart rate variability of the user is determined to correspond to the drink, transmitting a notification to a computing device of a user wearing the body-worn sensors, and polling the body-worn sensors for the additional data; and wherein when the at least one respiration rate, heart rate, or heart rate variability of the user does not correspond to the drink, polling the body-worn sensors for the additional data.

Statement 26: The non-transitory computer-readable storage medium according to Statement 25, wherein the determination of the drink motion is informed by contextual data; method further comprising: receiving contextual data; generating a variable contextual threshold based on the contextual data; identifying the received data as the drink motion when the contextual threshold is lower than a baseline value; and identifying the received data as a non-drink motion when the contextual threshold is greater than a baseline value.

Statement 27: The non-transitory computer-readable storage medium according to Statement 26, further comprising: determining if the user of the body-worn sensors is sleeping; and determining if the motion data corresponds to a known non-drink motion.

Statement 28: The non-transitory computer-readable storage medium of any one according to Statements 25-27, further comprising pre-processing the motion data using dynamic time warping.

Statement 29: The non-transitory computer-readable storage medium according to Statement 25, wherein the one or more body-worn sensors comprises at least one motion sensor and one or more biological sensors.

Statement 30: The non-transitory computer-readable storage medium according to Statement 29, wherein the at least one motion sensor includes at least one of an inertial motion unit, an accelerometer, a magnetometer, and a gyroscope.

Statement 31: The non-transitory computer-readable storage medium according to Statement 29, wherein the one or more biological sensors includes a photoplethysmography monitor, and the biological data comprises at least one of blood oxygen saturation data, heart rate data, heart rate variation data, blood pressure data, and respiration rate data.

Statement 32: The non-transitory computer-readable storage medium of any one according to Statements 25-31, further comprising processing at least one of the motion data and the biological data using a machine learning classification technique.

Statement 33: The non-transitory computer-readable storage medium of any one according to Statements 25-31, wherein the transmitted notification to the user comprises generating a graphic display.

Statement 34: The non-transitory computer-readable storage medium according to Statement 33, wherein the graphic display indicates a number of drinks taken by the user.

Statement 35: The non-transitory computer-readable storage medium according to Statement 33, wherein the graphic display indicates the user hydration level over time.

Statement 36: The non-transitory computer-readable storage medium according to Statement 25, wherein motion data, biological data, or both motion data and biological data are used to identify the drink.

Methods according to the above-described examples and statements can be implemented using computer-executable instructions that are stored or otherwise available from computer readable media. Such instructions can comprise, for example, instructions and/or data which cause and/or otherwise configure a general purpose computer, special purpose computer, or special purpose processing device to perform a certain function or group of functions. Portions of computer resources used can be accessible over a network. The computer executable instructions can be, for example, binaries, intermediate format instructions such as assembly language, firmware, and/or source code. Examples of computer-readable media that can be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals and/or add-in cards. Such functionality can also be implemented on a circuit board among different chips and/or different processes executing in a single device, by way of further example.

The instructions, media for conveying such instructions, computing resources for executing them, and/or other structures for supporting such computing resources are means for providing the functions described in these disclosures.

Although a variety of examples and/or other information was used to explain aspects within the scope of the appended claims, no limitation of the claims should be implied based on particular features and/or arrangements in such examples, as one of ordinary skill would be able to use these examples to derive a wide variety of implementations. Further and although some subject matter can have been described in language specific to examples of structural features and/or method blocks, it is to be understood that the subject matter defined in the appended claims is not necessarily limited to these described features and/or acts. For example, such functionality can be distributed differently and/or performed in components other than those identified herein. Rather, the described features and/or blocks are disclosed as examples of components of systems and/or methods within the scope of the appended claims.

It will be appreciated that variations of the above-disclosed and/or other features and/or functions, or alternatives thereof, can be desirably combined into many other different systems and/or applications. Also that various presently unforeseen or unanticipated alternatives, modifications, variations or improvements therein can be subsequently made by those skilled in the art which are also intended to be encompassed by the following claims.

What is claimed is:

1. A system for contextual drink detection for a user wearing one or more body-worn sensors, the system comprising:
a memory; and
at least one processor to:
receive data from the one or more body-worn sensors;

determine if the received data includes motion data or biological data;

wherein when the received data includes motion data, the processor to:
- classify the motion data as a pre-determined motion pattern;
- determine if the classified pre-determined motion pattern corresponds to a drink;
- wherein when the classified pre-determined motion pattern is identified as the drink, the processor to tally the drink, transmit a notification to a computing device of a user wearing the body-worn sensors, and poll the body-worn sensors for additional data; and
- wherein when the classified pre-determined motion pattern is not identified as the drink, the processor to poll the body-worn sensors for the additional data; and wherein when the received data includes biological data, the processor to:
- determine at least one of a respiration rate, heart rate, or heart rate variability of the user;
- determine if the at least one respiration rate, heart rate, or heart rate variability of the user corresponds to the drink;
- wherein when the at least one respiration rate, heart rate, or heart rate variability of the user corresponds to the drink, the processor to tally the drink, transmit a notification to a computing device of a user wearing the body-worn sensors, and poll the body-worn sensors for the additional data; and
- wherein when the at least one respiration rate, heart rate, or heart rate variability of the user does not correspond to the drink, the processor to poll the body-worn sensors for the additional data;

record the tally of the drink to an input log for drink events;

determine, based on a balancing of the input log for recorded drinks and an output log for expelled fluids, each of the input log and the output log being based on data received from the one or more body-worn sensors, a net hydration balance for the user;

determine whether the net hydration balance is within a predetermined hydration range; and when the net balance of hydration is not within the predetermined hydration range, transmit a notification to the user.

2. The system of claim 1, wherein the determination of the drink motion is informed by contextual data and the system further comprising:
the processor to:
- receive contextual data;
- generate a variable contextual threshold based on the contextual data;
- wherein the received data is more likely to be identified as the drink motion when the contextual threshold is lower than a baseline value; and
- wherein the received data is less likely to be identified as the drink motion when the contextual threshold is greater than a baseline value.

3. The system of claim 2, further comprising:
the processor to:
- determine if the user of the body-worn sensors is sleeping; and
- determine if the motion data corresponds to a known non-drink motion.

4. The system of claim 1, wherein the motion data is pre-processed using dynamic time warping.

5. The system of claim 1, wherein the one or more body-worn sensors comprises at least one motion sensor and one or more biological sensors.

6. The system of claim 5, wherein the at least one motion sensor includes at least one of an inertial motion unit, an accelerometer, a magnetometer, and a gyroscope.

7. The system of claim 5, wherein the one or more biological sensors includes a photoplethysmography monitor, and the biological data comprises at least one of blood oxygen saturation data, heart rate data, heart rate variation data, blood pressure data, and respiration rate data.

8. The system of claim 1, wherein at least one of the motion data and the biological data is processed by a machine learning classification technique.

9. The system of claim 1, wherein the transmitted notification to the user comprises a graphic display.

10. The system of claim 9, wherein the graphic display indicates a number of drinks taken by the user.

11. The system of claim 9, wherein the graphic display indicates the user hydration level over time.

12. The system of claim 1, wherein motion data, biological data, or both motion data and biological data are used to identify the drink.

13. A method for contextual drink detection of a user wearing one or more body-worn sensors; the method comprising:
receiving, by at least one processor, data from the one or more body-worn sensors;
determining, by the at least one processor, if the received data includes motion data or biological data;
wherein when the received data includes motion data:
- classifying, by at least one processor, the motion data as a pre-determined motion pattern;
- determining, by the at least one processor, if the classified pre-determined motion pattern corresponds to a drink;
- wherein when the classified pre-determined motion pattern is identified as the drink by the at least one processor, tallying the drink, transmitting a notification to a computing device of a user wearing the body-worn sensors, and polling the body-worn sensors for additional data; and
- wherein the classified pre-determined motion pattern is not identified as the drink by the at least one processor, polling the body-worn sensors for the additional data; and wherein when the received data includes biological data:
- determining, by the at least one processor, at least one of a respiration rate, heart rate, or heart rate variability of the user;
- determining, by the at least one processor, if the at least one of a respiration rate, heart rate, or heart rate variability corresponds to the drink motion;
- wherein when the at least one respiration rate, heart rate, or heart rate variability of the user is determined to correspond to the drink by the at least one processor, tallying the drink, transmitting a notification to a computing device of a user wearing the body-worn sensors, and polling the body-worn sensors for the additional data; and
- wherein when the at least one respiration rate, heart rate, or heart rate variability of the user is determined not to correspond to the drink by the at least one processor, polling the body-worn sensors for the additional data;

recording the tally of the drink to an input log for drink events;

determining, based on a balancing of the input log for recorded drinks and an output log for expelled fluids, each of the input log and the output log being based on data received from the one or more body-worn sensors, a net hydration balance for the user;

determining whether the net hydration balance is within a predetermined hydration range; and when the net balance of hydration is not within the predetermined hydration range, transmitting a notification to the user.

14. The method of claim 13, wherein the determination of the drink motion is informed by contextual data; method further comprising:

receiving, by the at least one processor, contextual data;

generating, by the at least one processor, a variable contextual threshold based on the contextual data;

identifying, by the at least one processor, the received data as the drink motion when the contextual threshold is lower than a baseline value; and identifying, by the at least one processor, the received data as a non-drink motion when the contextual threshold is greater than a baseline value.

15. The method of claim 14, further comprising:

determining, by the at least one processor, if the user of the body-worn sensors is sleeping; and determining, by the at least one processor, if the motion data corresponds to a known non-drink motion.

16. The method of claim 13, further comprising pre-processing, by the at least one processor, the motion data using dynamic time warping.

17. The method of claim 13, wherein the one or more body-worn sensors comprises at least one motion sensor and one or more biological sensors.

18. The method of claim 17, wherein the at least one motion sensor includes at least one of an inertial motion unit, an accelerometer, a magnetometer, and a gyroscope.

19. The method of claim 17, wherein the one or more biological sensors includes a photoplethysmography monitor, and the biological data comprises at least one of blood oxygen saturation data, heart rate data, heart rate variation data, blood pressure data, and respiration rate data.

20. The method of claim 13, further comprising processing, by the at least one processor, at least one of the motion data and the biological data using a machine learning classification technique.

21. The method of claim 13, wherein the transmitted notification to the user comprises generating, by the at least one processor, a graphic display.

22. The method of claim 21, wherein the graphic display indicates a number of drinks taken by the user.

23. The method of claim 21, wherein the graphic display indicates the user hydration level over time.

24. The method of claim 13, wherein motion data, biological data, or both motion data and biological data are used to identify the drink.

25. A non-transitory computer-readable storage medium, having instructions for contextual drink detection stored thereon that, when executed by a computing device cause the computing device to perform operations, the operations comprising:

receiving data from one or more body-worn sensors;

determining if the received data includes motion data or biological data;

wherein when the received data includes motion data:

classifying the motion data as a pre-determined motion pattern;

determining if the classified pre-determined motion pattern corresponds to a drink;

wherein the classified pre-determined motion pattern is identified as the drink by at least one processor, tallying the drink, transmitting a notification to a computing device of a user wearing the body-worn sensors, and polling the body-worn sensors for additional data; and wherein when the classified pre-determined motion pattern is not identified as the drink by the at least one processor, polling the body-worn sensors for the additional data; and wherein when the received data includes biological data:

determining at least one of a respiration rate, heart rate, or heart rate variability of the user;

determining if the at least one of a respiration rate, heart rate, or heart rate variability corresponds to the drink motion;

wherein when the at least one respiration rate, heart rate, or heart rate variability of the user is determined to correspond to the drink, transmitting a notification to a computing device of a user wearing the body-worn sensors, and polling the body-worn sensors for the additional data; and wherein when the at least one respiration rate, heart rate, or heart rate variability of the user does not correspond to the drink, polling the body-worn sensors for the additional data;

recording the tally of the drink to an input log for drink events;

determining, based on a balancing of the input log for recorded drinks and an output log for expelled fluids, each of the input log and the output log being based on data received from the one or more body-worn sensors, a net hydration balance for the user;

determining whether the net hydration balance is within a predetermined hydration range; and when the net balance of hydration is not within the predetermined hydration range, transmitting a notification to the user.

26. The non-transitory computer-readable storage medium of claim 25, wherein the determination of the drink motion is informed by contextual data; method further comprising:

receiving contextual data;

generating a variable contextual threshold based on the contextual data;

identifying the received data as the drink motion when the contextual threshold is lower than a baseline value; and identifying the received data as a non-drink motion when the contextual threshold is greater than a baseline value.

27. The non-transitory computer-readable storage medium of claim 26, further comprising:

determining if the user of the body-worn sensors is sleeping; and determining if the motion data corresponds to a known non-drink motion.

28. The non-transitory computer-readable storage medium of claim 25, further comprising pre-processing the motion data using dynamic time warping.

29. The non-transitory computer-readable storage medium of claim 25, wherein the one or more body-worn sensors comprises at least one motion sensor and one or more biological sensors.

30. The non-transitory computer-readable storage medium of claim 29, wherein the at least one motion sensor includes at least one of an inertial motion unit, an accelerometer, a magnetometer, and a gyroscope.

31. The non-transitory computer-readable storage medium of claim 29, wherein the one or more biological sensors includes a photoplethysmography monitor, and the biological data comprises at least one of blood oxygen saturation data, heart rate data, heart rate variation data, blood pressure data, and respiration rate data.

32. The non-transitory computer-readable storage medium of claim 25, further comprising processing at least one of the motion data and the biological data using a machine learning classification technique.

33. The non-transitory computer-readable storage medium of claim 25, wherein the transmitted notification to the user comprises generating a graphic display.

34. The non-transitory computer-readable storage medium of claim 33, wherein the graphic display indicates a number of drinks taken by the user.

35. The non-transitory computer-readable storage medium of claim 33, wherein the graphic display indicates the user hydration level over time.

36. The non-transitory computer-readable storage medium of claim 25, wherein motion data, biological data, or both motion data and biological data are used to identify the drink.

* * * * *